United States Patent
Van Damme et al.

(10) Patent No.: US 9,968,336 B2
(45) Date of Patent: May 15, 2018

(54) LIQUID SAMPLER, KIT OF PARTS, AND METHOD FOR ASSEMBLY

(71) Applicant: NOVOSANIS NV, Antwerp (BE)

(72) Inventors: Pierre Van Damme, Kontich (BE); Alex Vorsters, Borgerhout (BE); Vanessa Vankerckhoven, Wilrijk (BE); Stijn Verwulgen, Schoten (BE); Christiaan Baelus, Antwerp (BE); Lara Biekens, Kapellen (BE); Koen Beyers, Wuustwezel (BE); Kristof Sorgeloos, Beveren-waas (BE); Hanne De Bauw, Antwerp (BE)

(73) Assignee: NOVOSANIS NV, Antwerp (BE)

( * ) Notice: Subject to any disclaimer, the term of this patent is extended or adjusted under 35 U.S.C. 154(b) by 259 days.

(21) Appl. No.: 14/427,092

(22) PCT Filed: Jul. 26, 2013

(86) PCT No.: PCT/EP2013/065853
§ 371 (c)(1),
(2) Date: Mar. 10, 2015

(87) PCT Pub. No.: WO2014/037152
PCT Pub. Date: Mar. 13, 2014

(65) Prior Publication Data
US 2015/0223784 A1    Aug. 13, 2015

(30) Foreign Application Priority Data

Sep. 10, 2012  (GB) .................................. 1216079.2

(51) Int. Cl.
*A61F 5/44* (2006.01)
*B01L 3/00* (2006.01)
(Continued)

(52) U.S. Cl.
CPC ........ *A61B 10/007* (2013.01); *A61B 5/14507* (2013.01); *A61F 5/4405* (2013.01);
(Continued)

(58) Field of Classification Search
CPC .............. A61B 10/007; A61B 5/14507; G01N 1/2035; G01N 1/20; G01N 1/16; B01L 3/502; B01L 3/505
(Continued)

(56) References Cited

U.S. PATENT DOCUMENTS 3,894,845 A * 7/1975 McDonald ........... A61B 10/007
422/430
4,305,405 A * 12/1981 Meisch .................... A61B 5/20
53/157
(Continued)

FOREIGN PATENT DOCUMENTS

CN        1420750 A      5/2003
CN     101583316 A     11/2009
(Continued)

OTHER PUBLICATIONS

Chinsese Search Report from Chinese Application No. 201380047160.5, dated Aug. 23, 2016.
(Continued)

*Primary Examiner* — R. A. Smith
*Assistant Examiner* — John M Royston
(74) *Attorney, Agent, or Firm* — Workman Nydegger

(57) ABSTRACT

A device for capturing a predetermined volume of a predefined portion (e.g. first void) of a liquid flow, comprises an inlet, an outlet, and a guide with an element displaceable in a first position for capturing the first liquid portion in a reservoir, and in a second position for blocking access to the reservoir, and for passing the liquid to the outlet. The displaceable element moves in transverse direction to the
(Continued)

liquid flow, and has lifting means. The element may be substantially flat, or tubular with an elliptical cross section. A kit of parts and a method of assembly are also claimed.

20 Claims, 17 Drawing Sheets

(51) Int. Cl.

| | | |
|---|---|---|
| G01N 1/16 | (2006.01) | |
| G01N 1/20 | (2006.01) | |
| A61B 10/00 | (2006.01) | |
| A61B 5/145 | (2006.01) | |

(52) U.S. Cl.
CPC ........ *G01N 1/2035* (2013.01); *A61B 2562/12* (2013.01); *B01L 3/502* (2013.01); *B01L 3/505* (2013.01); *G01N 1/16* (2013.01); *G01N 1/20* (2013.01); *Y10T 29/49826* (2015.01)

(58) Field of Classification Search
USPC ...... 73/863.41, 863.42, 864, 864.33, 864.51, 73/864.63, 864.91; 422/559, 560
See application file for complete search history.

(56) References Cited

U.S. PATENT DOCUMENTS

| | | | |
|---|---|---|---|
| 4,494,581 A | 1/1985 | Gordon | |
| 5,105,824 A | 4/1992 | Rasch | |
| 5,622,183 A * | 4/1997 | Hazard | A61B 10/007 |
| | | | 4/144.2 |
| 5,785,044 A * | 7/1998 | Meador | A61B 10/007 |
| | | | 206/221 |
| 7,435,242 B2 | 10/2008 | Levinson | |
| 7,819,821 B2 | 10/2010 | Forte et al. | |
| 8,328,733 B2 | 12/2012 | Forte et al. | |
| 2003/0149408 A1 | 8/2003 | Levinson | |
| 2008/0228106 A1 | 9/2008 | Forte et al. | |
| 2009/0048568 A1 | 2/2009 | Levinson | |
| 2011/0040272 A1 | 2/2011 | Forte et al. | |
| 2011/0237977 A1 | 9/2011 | Knight et al. | |

FOREIGN PATENT DOCUMENTS

| | | |
|---|---|---|
| GB | 1574864 A | 9/1980 |
| JP | S6479658 A | 3/1989 |
| WO | 2004010873 A1 | 2/2004 |
| WO | 2004043264 A1 | 5/2004 |
| WO | 2005003725 A2 | 1/2005 |
| WO | 2005107602 A1 | 11/2005 |
| WO | 2008065325 A1 | 6/2008 |
| WO | 2011140600 A1 | 11/2011 |
| WO | 2014037152 A1 | 3/2014 |

OTHER PUBLICATIONS

Chinese Office Action from Chinese Application No. 201380047160.5, dated Sep. 2, 2016.
Great Britain Search Report for corresponding Great Britain Application No. 1216079.2, dated Dec. 12, 2012.
International Search Report for corresponding International PCT Application No. PCT/EP2013/065853, dated Sep. 20, 2013.
Netherlands Search Report from Netherlands Application No. NL2011416, dated Jun. 17, 2014.

* cited by examiner

FIG.8
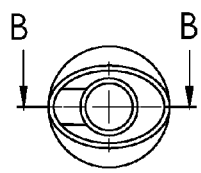
FIG.10  FIG.11  FIG.9
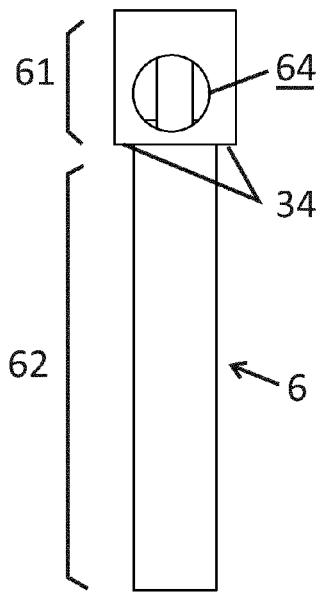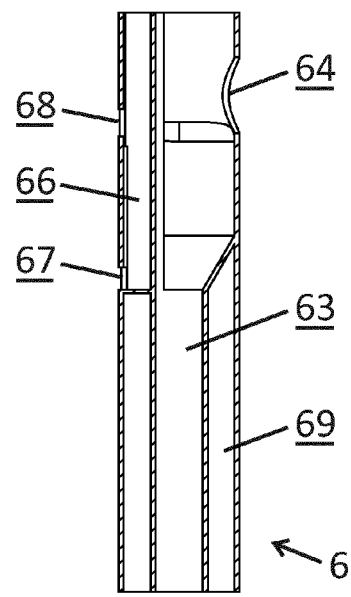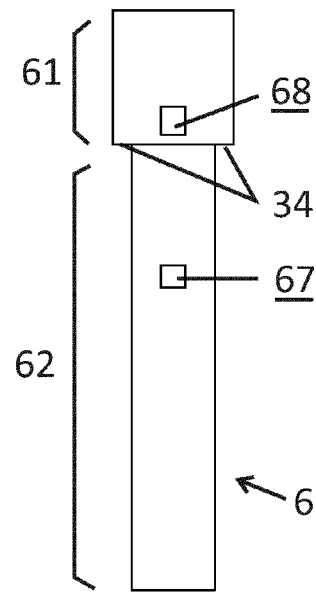
SECTION B-B
FIG.7
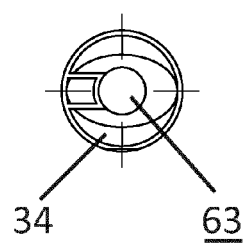

SECTION A-A

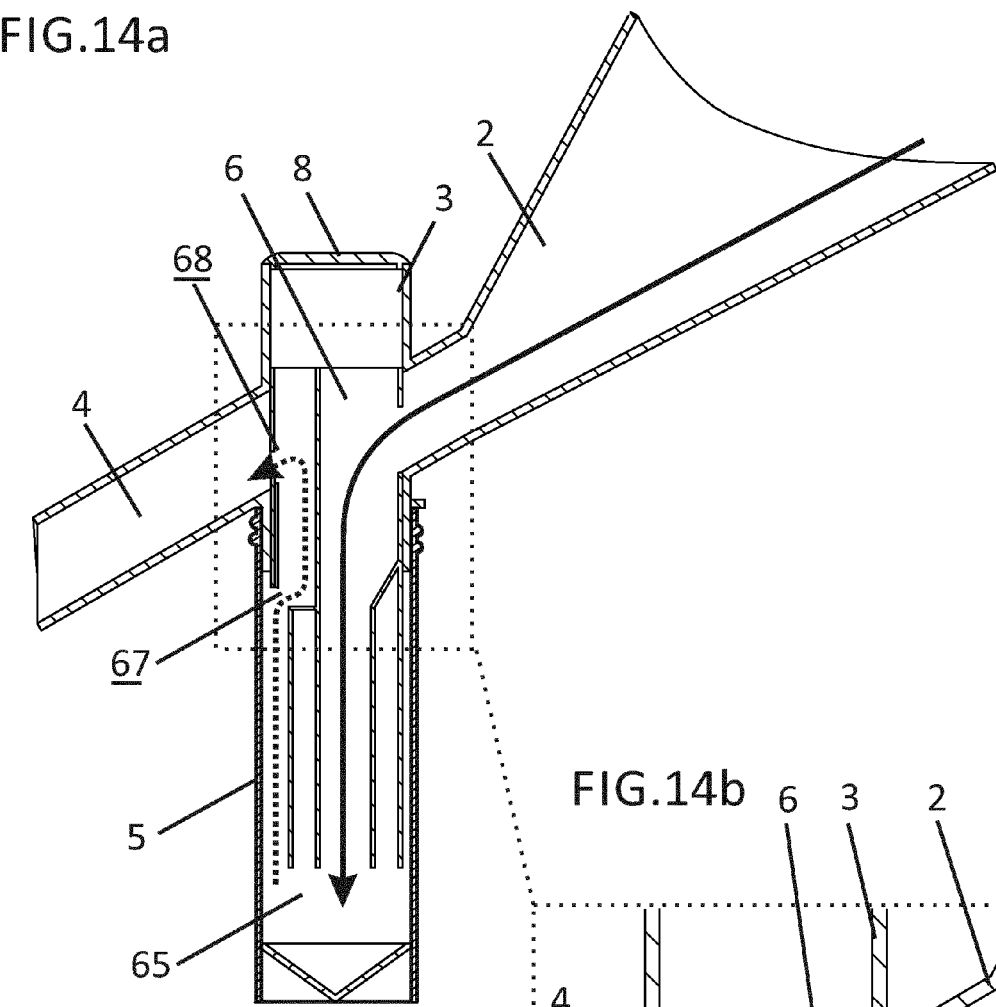
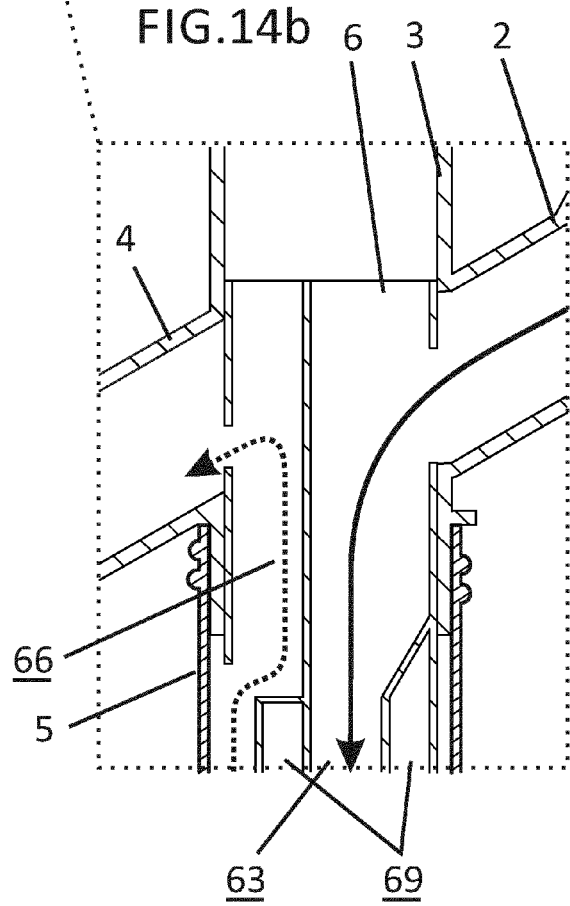

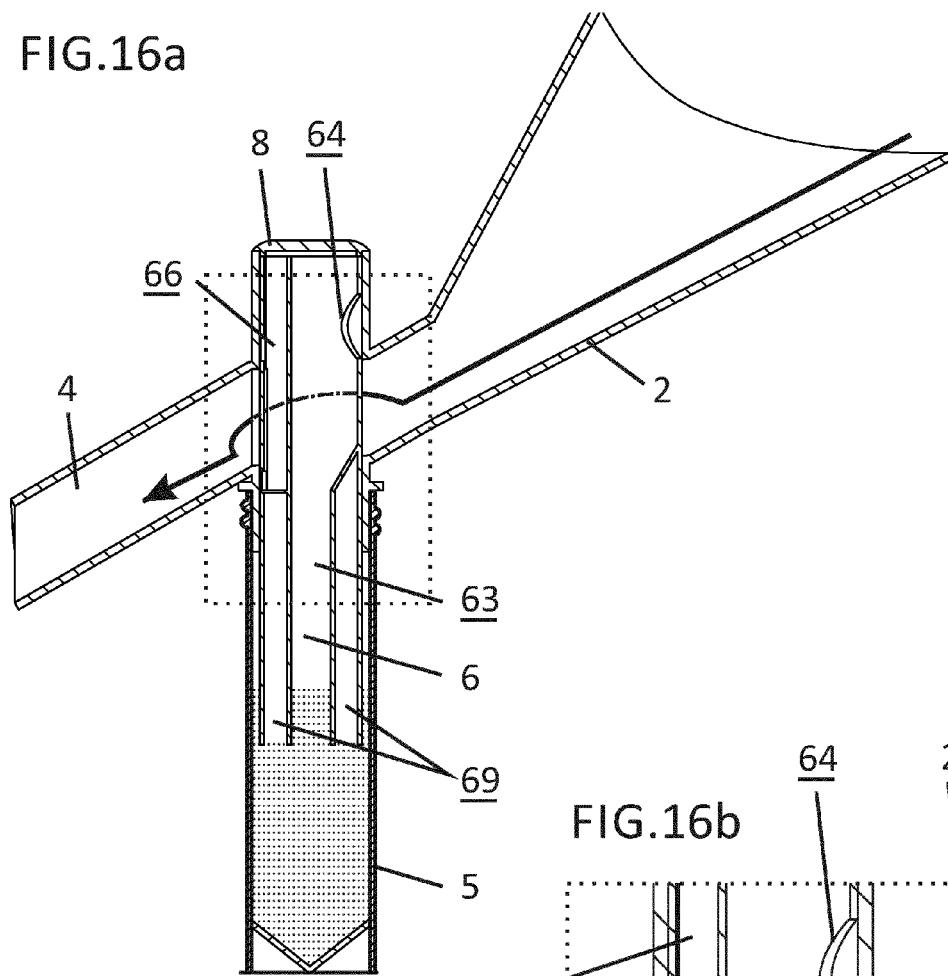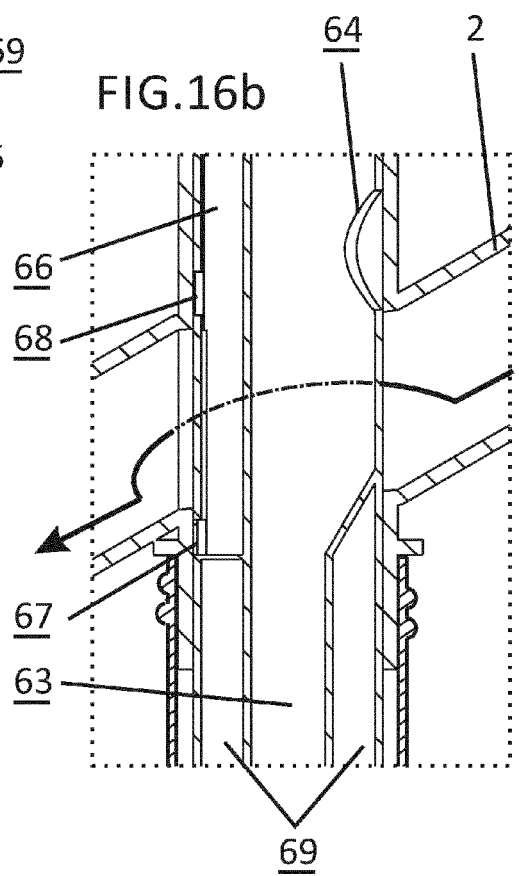

SECTION A-A

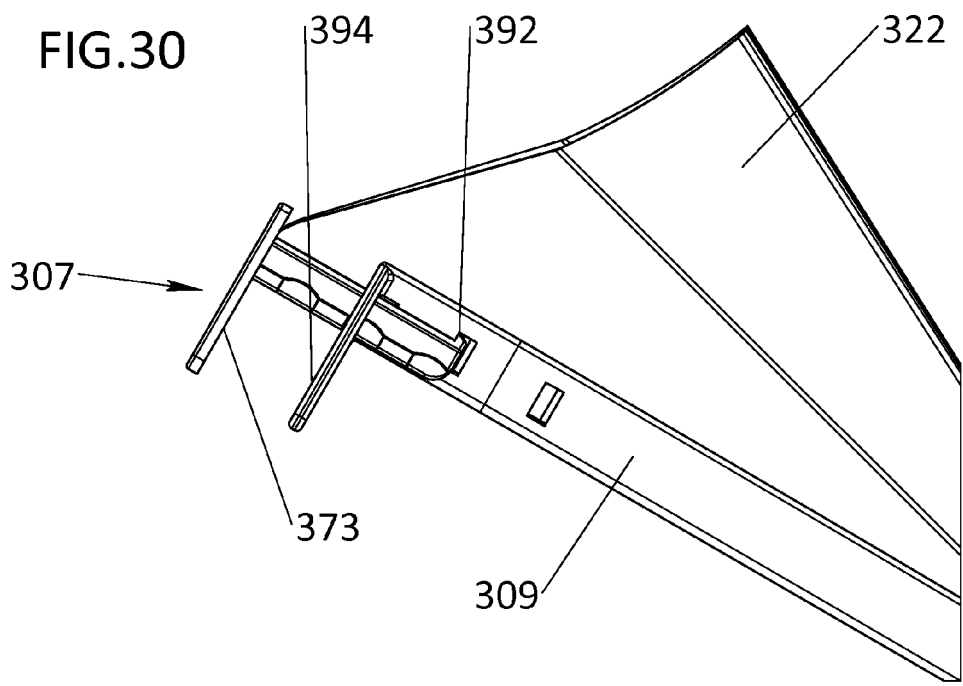
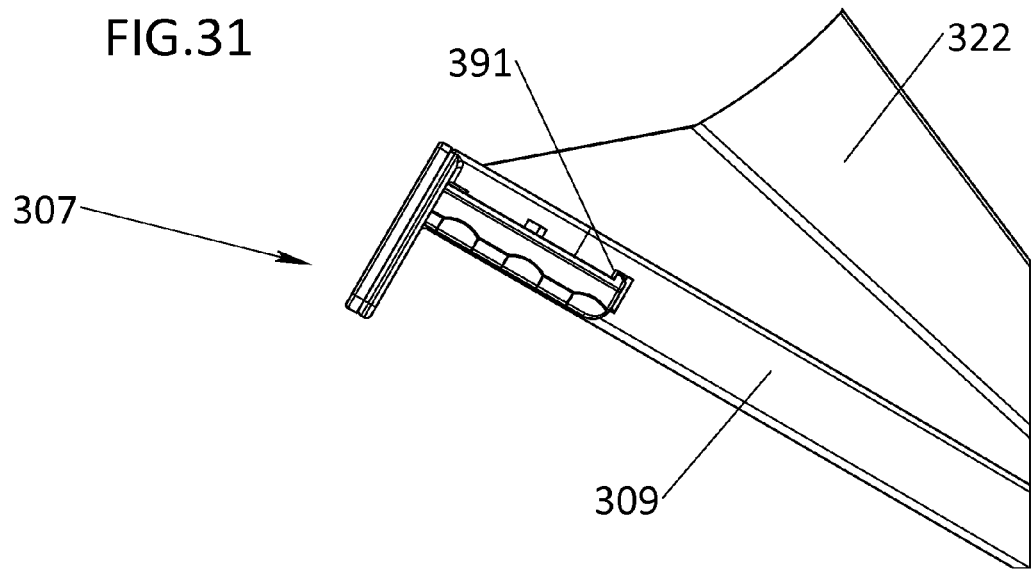

LIQUID SAMPLER, KIT OF PARTS, AND METHOD FOR ASSEMBLY

FIELD OF THE INVENTION

The present invention relates to the field of liquid collection devices, more particularly to the field of devices for capturing a predetermined volume of a predefined portion (e.g. first void, mid-stream, other fraction) of a liquid flow.

BACKGROUND OF THE INVENTION

Advances in clinical molecular diagnostics have led to sensitive DNA detection assays for testing Chlamydia, gonorrhoea and other sexually transmitted infections (STI) such as human papilloma virus (HPV). Some of these assays are already used on urine samples. Major advantage of a urine sample is that it can be relatively easily obtained by a non-invasive self-sampling method in all age groups and by both genders. For STI diagnosis the first void urine fraction, which is undiluted by mid-stream urine, is recommended for analysis as it contains the highest concentration of DNA of the pathogen. When testing urine, deterioration of DNA should be prevented by adding nuclease inhibitors or chaotropic agents. For other tests on urine such as diagnosing urinary tract infections (UTIs), biochemistry, and monitoring the progression of diseases such as diabetes mellitus and high blood pressure (hypertension) a more sterile fraction, e.g. mid-stream urine that is not contaminated by first void urine, should be isolated.

Urine samples are typically collected in a small container, which makes sampling difficult for males, but especially for females. In case a specific fraction of urine e.g. first void urine is needed, the urine stream needs to be interrupted leading to a messy experience for the user and very often inaccurate sampling of urine.

Also for various other purposes, e.g. drug tests; testing for doping in sport, urine collection is needed, preferable to take place in hygienic circumstances imposing minimal challenges to the subject.

Devices for capturing a first portion of urine are known in the art. WO2004/010873 discloses a liquid sampler where the liquid enters at an inlet. The sample passes through a valve into a sample chamber and then the valve closes, diverting the remainder of the liquid flow to a sampler overflow. As mentioned by the authors of this application a drawback of the sampler is that the sample collected may become diluted by liquid or urine delivered later in the liquid flow or the urine specimen. This dilution depends on the speed of operation, and the effectiveness of the valve action, and may also depend on the rate of delivery of the liquid flow or the urine sample.

SUMMARY OF THE INVENTION

It is an object of embodiments of the present invention to provide a good method and device for capturing a predefined portion of a liquid flow.

In particular, it is an object of embodiments of the present invention to provide a method and device for automatically capturing a predetermined volume of a predefined part of a liquid stream.

This objective is accomplished by a method and device and kit of parts, according to embodiments of the present invention.

In a first aspect, the present invention provides a device for capturing a first portion of a liquid flow, the device comprising: an inlet for receiving the liquid flow; an outlet for draining an excess of the liquid flow, e.g. in particular while the liquid is flowing; a guide connected between the inlet and the outlet, and adapted for directing the first portion of the liquid flow towards a reservoir connected to the guide and for directing a subsequent portion of the liquid flow to the outlet; wherein the guide comprises a displaceable element adapted for creating passage of liquid between the inlet and the reservoir while blocking passage of liquid between the inlet and the outlet when the element is in a first position, and for blocking passage of liquid between the inlet and the reservoir while creating passage of liquid between the inlet and the outlet when the element is in a second position, the element comprising lifting means for displacing the element from the first to the second position when the first portion of the liquid flow is captured in the reservoir.

It is an advantage of using a displaceable element rather than a valve with a specific diameter, because it allows the first liquid portion to flow substantially unhindered (i.e. at full speed) to the reservoir, so that the risk of mixing the first liquid portion with a second liquid portion before the first portion has reached the reservoir is drastically reduced, if not completely eliminated.

It is a further advantage of using the displaceable element in that it can completely block further entrance of liquid once a predetermined amount of the first liquid portion is collected. This drastically reduces or completely eliminates the risk of mixing the first liquid portion already captured in the reservoir with subsequent liquid portions.

Using a displaceable element rather than surface tension for closing the reservoir is advantageous, as it provides mechanical blockage.

It is an advantage of a device according to embodiments of the present invention that it can be easily dimensioned to capture a predefined amount of the first liquid portion, substantially independent of the flow rate, which may vary between wide ranges (e.g. from 1 ml/sec to 55 ml/sec).

It is an advantage of a device according to embodiments of the present invention to have an outlet suitable for draining an excess of the liquid flow, in particular while the liquid is still flowing, as opposed to some prior art devices, where first the entire amount of liquid is collected in the device, which device then has to be tilted for removing the excess of liquid. It is much easier with the device of the present invention to avoid spillage.

In a device according to embodiments of the present invention, the displaceable element is an elongated element movable in a direction substantially transverse to the direction from the inlet to the outlet.

It is advantageous to move the displaceable element in a direction substantially transverse to the direction of the liquid stream, e.g. perpendicular thereto or within a deviation from this perpendicular direction of not more than 55°, because such movement is not substantially counteracted by the liquid flow, thus the force required for moving the element in such direction are reduced.

It is an advantage of the device that the flow friction is reduced, e.g. minimized at several stages thus ensuring improved flow capacity, while avoiding congestions, overflow and spillage. This also allows improved mixing with a substance which may optionally be present in the reservoir before the liquid capture, which mixing is independent of the flow rate and variations in flow rate.

In a device according to embodiments of the present invention, the lifting means comprises a predefined volume of a material having a mass density lower than that of the liquid to be captured.

By using such low mass density material (relative to the mass density of the liquid to be captured), lifting of the displaceable element is obtained automatically while fluid is being collected.

A suitable material for capturing a liquid having a mass density of at about 0.90 to 1.10 kg/dm$^3$, such as e.g. urine is e.g. low density foam, e.g. Styrofoam®. When this material is submerged in such a liquid, the element will be lifted due to the Archimedes force. The required amount of said material depends primarily on the weight of the movable element, and is substantially independent on the amount of liquid to be captured.

In a device according to embodiments of the present invention, the lifting means comprise at least one air chamber.

It is an advantage of using an air chamber as lifting means, in that it is very lightweight, and does not require extra material cost, and does not have to be disposed after use of the device.

When using an air chamber, the need for the lightweight material (e.g. the foam) mentioned above can be omitted.

An air chamber and low density material may be used each per se, or in combination.

In a device according to embodiments of the present invention, the inlet is a tubular inlet and/or the outlet is a tubular outlet.

A tubular inlet and/or outlet may be provided for ease of use of the device. A tubular inlet and/or outlet reduces the chances of spillage of fluid.

In a device according to embodiments of the present invention, the displaceable element has at least a first segment with a first cross section, and a second segment with a second cross section smaller than the first cross section, and a first channel extending from a first opening in the first segment to a second opening in the second segment, such that when the element is in the first position the first opening is in fluid connection with the inlet for receiving the first portion of the liquid flow so as to direct the first portion through the first channel towards the reservoir, and such that when the element is in the second position the first opening is blocked from the inlet while the smaller cross section of the second segment allows passage of the second fluid portion from the inlet to the outlet; and the guide has an internal edge complementary to the second cross section.

The element may have at least two segments, for example two segments, in which case they can called "upper segment" and "lower segment", or more than two segments, e.g. three.

The cross-section is taken in a plane perpendicular to a longitudinal axis of the displaceable element. It is an advantage of this arrangement that the first liquid portion cannot stream in a different way than into the first opening and into the first channel, and when the element is in its first, e.g. upper position, to bypass the element sideways towards the outlet.

It is an advantage of using a first channel without any internal protrusions, or without moving parts, in that the liquid flowing into the reservoir is not hindered, and no downward directed forces are exerted upon the displaceable element, so that it can easily move upwards. The inlet flow is not hampered by any obstacles and there are only minimal downwards forces exercised on the displaceable element by the incoming liquid stream that could hamper its upwards movement.

When the displaceable element moves upwards, the inlet is closed substantially without counteracting forces, either caused by the liquid stream, or by the weight of the amount of liquid column above the reservoir, which would also be lifted.

Since the entrance to the first channel is blocked, the risk for mixing with further liquid is impossible. The mechanism is based on allowing a first volume of liquid, independent of the flow rate of the liquid.

It is an advantage that the first opening moves upwards (not downwards), in that further supply of liquid into the first channel is prevented, while some air can still be drawn into the first channel, so that the liquid in the first channel can flow into the reservoir, instead of remaining in the first channel because of under-pressure, which may otherwise exist once the first opening is closed. This avoids spillage when the reservoir is removed after the liquid sampling.

It is an advantage of the internal edge of the guide that it has a shape complementary to that of the second cross section for preventing liquid to flow to the reservoir via the internal edge. It is a further advantage of this edge that, during assembly, the element can be inserted via the top and can rest on this edge without falling out of the device, e.g. on the ground. It is a further advantage that the displaceable element can again rest of this edge when the reservoir is removed from the guide, again preventing the element from falling out, e.g. on the ground.

In a device according to embodiments of the present invention, the cross-section of the first segment is circular, and the cross section of the second segment is elliptical, and wherein the guide has a corresponding elliptical edge.

Although a circular and an elliptical shape is not mandatory, a smooth surface is advantageous, in that it allows easy passage of the second and further portions of the liquid stream towards the outlet, when the element is moved to its second (upper) position, and a bypass channel is formed between the internal walls of the guide and the second segment. By allowing the second portion of the liquid to flow away, the risk of mixing with the first fraction is minimal and the user's convenience is largely increased. (minimal risk of spillage, and no control of the bladder is required in case of urine collection).

An additional advantage of using an elliptical shape instead of a smaller circular shape, is that the risk of rotation of the element around its axis is easily eliminated.

In a device according to embodiments of the present invention, the displaceable element further comprises a second channel arranged for allowing air to escape from the reservoir into the outlet during capturing of at least a fraction of the first portion of the liquid flow when the element is in the first position, and arranged such that passage of liquid from the outlet to the reservoir is blocked when the element is in the second position.

This second channel may comprise a third and a fourth opening. Alternatively, the second channel may comprise a gutter, a trench or a groove.

It is an advantage that the air in the reservoir can escape through a second channel different from the first channel, so that the flow created by the escaping air when the liquid enters the reservoir is not hampering the incoming liquid stream. In this way, the incoming liquid can be captured at even higher flow rates.

It is an advantage that the second channel (for air discharge) is integrated in the movable element, so that it is also automatically opened and closed in the first resp. second element position.

It is an advantage that the second channel (air channel) is blocked by an upper part of the guide when the movable element is in its second (upper) position, as it is an extra mechanism preventing the flow entering the reservoir.

In a device according to embodiments of the present invention, the guide has a first opening arranged between the inlet and the reservoir, and the element has a protrusion adapted for blocking the first opening when in the second position while leaving the first opening open when in the first position for receiving the first fluid portion; the displaceable element has an upper segment with a closed wall section and a lower segment with a narrowing or a second opening arranged such that the closed wall section blocks passage of liquid from the inlet to the outlet when in the first position for directing the first fluid portion towards the reservoir, while allowing passage of the second fluid portion from the inlet to the outlet when in the second position.

It is an advantage of this arrangement that the first liquid portion cannot stream in a different way than into the first opening, and when the element is in its upper position, to bypass the element towards the outlet.

Since the entrance to the first opening is mechanically blocked when the required amount of liquid is captured in the reservoir, the risk for mixing with further liquid is drastically reduced. The mechanism is based on allowing a first volume of liquid, independent of the flow rate of the liquid.

In a device according to embodiments of the present invention, the upper segment and the lower segment of the displaceable element are substantially planar.

It is an advantage of this embodiment that it requires less material, and is easier to produce.

In an embodiment, the device further comprises a second guide and a second movable element and a second reservoir for capturing a second portion of the liquid stream.

The first guide and first movable element and first reservoir may be identical in shape and/or dimension to the second guide resp. the second movable element and the second reservoir, or may be different.

In an embodiment, the device further comprises a cap for closing an upper part of the guide.

Although not absolutely required for correct functioning of the device, this may help to avoid spillage during and after capturing of the liquid sample. It may also reduce the risk of incorrect use of the device (e.g. using the guide opening instead of the input channel).

In a device according to embodiments of the present invention, the inlet comprises a funnel.

Preferably, in case of urine collection, the funnel is shaped to allow use by both genders. Alternatively, different funnels can be used for men and women. The funnel may be part of the inlet, or may be a separate part mountable thereto. In the latter case, the inlet preferably comprises a funnel support whereto the funnel can be mounted.

In a device according to embodiments of the present invention, the funnel is made of a material which can be reversibly folded and unfolded or reversibly snap-compressed and decompressed.

It is an advantage that the volume of the funnel can be reduced without damaging it, to allow shipment via regular mail.

A device according to embodiments of the present invention may further comprise a clip for holding the funnel to the funnel support, and/or for holding the funnel in an unfolded or decompressed state, and/or for positioning the device to stand in an upright position on a substantially horizontal surface.

It is an advantage of such a clip that it can hold the funnel in an "open" position for easy collection of the liquid. Such a clip is convenient for the user as he/she does not have to exert forces on the funnel to keep it "open", and thus the risk of spillage is reduced.

Such a clip may also be used to allow the device to be placed in an upright position on a substantially horizontal surface. It is an advantage of such a device that the reservoir can be positioned with its opening directed upwards, before and/or after use. In this way, even when being slightly tilted, the content of the reservoir, e.g. a preservation liquid (before use) or a urine sample (after use), will remain in the reservoir when the device is (temporarily) placed on the surface, e.g. on a table.

In a device according to embodiments of the present invention, the device is at least partly made of biologically degradable material.

Preferably the device is completely made of such material, except for the reservoir, which may be sent back to a lab.

In a device according to embodiments of the present invention, the inlet, the outlet and the guide are combined or assembled in a monolithic part.

Using less parts simplifies the assembly by the end user.

In a device according to embodiments of the present invention, the inlet, the outlet and the guide are made from polymers, preferably selected from the group consisting of polypropylene and polyethylene, or from biological degradable materials.

Polypropylene is found to be a very suitable material for this application, especially because of its rigidity during transport and its folding capacity, allowing to provide breakproof integrated hinges based on folding lines.

In a device according to embodiments of the present invention, the device or separable parts thereof have dimensions such as to fit in a box of 380 mm×265 mm×32 mm.

It is an advantage that such a device can be delivered by regular mail.

In a second aspect, the present invention provides a kit of parts, comprising: a tubular inlet; a tubular outlet; a guide having at least three openings, a first opening connectable to the tubular inlet, a second opening connectable to the tubular outlet, a third opening connectable to a reservoir; an element displaceable in the guide, and adapted for creating passage for liquid between the inlet and the reservoir while blocking passage of liquid between the inlet and the outlet when the element is in a first position, and for blocking passage of liquid between the inlet and the reservoir while creating passage for liquid between the inlet and the outlet in a second position, the element comprising lifting means.

In a kit of parts according to embodiments of the present invention, two or more of the tubular inlet and the tubular outlet and the guide are combined or assembled in a monolithic part.

A kit of parts according to embodiments of the present invention may further comprise a reservoir.

In an embodiment, the reservoir has a volume of 1 to 750 ml, preferably from 1 to 50 ml, more preferably from 1 to 15 ml, most preferably from 3 to 15 ml, depending on the application.

In an embodiment, the reservoir comprises a DNA stabilization agent, or a preservation liquid.

The agent may be a solid or a liquid substance.

A kit of parts according to embodiments of the present invention may further comprise a funnel and a clip for mounting the funnel to the inlet of the guide.

In a third aspect, the present invention provides a method for assembling the device, the method comprising: —providing a guide adapted for directing a first portion of a liquid flow towards a reservoir connected to the guide and for directing a subsequent portion of the liquid flow to an outlet; —if the inlet is separate from the guide, connecting the inlet to the guide; —if the outlet is separate from the guide, connecting the outlet to the guide; —connecting the reservoir to the guide; —inserting the displaceable element in the guide, the displaceable element being adapted for creating passage of liquid between the inlet and the reservoir while blocking passage of liquid between the inlet and the outlet when the displaceable element is in a first position in the guide, and for blocking passage of liquid between the inlet and the reservoir while creating passage of liquid between the inlet and the outlet when the displaceable element is in a second position in the guide.

In an embodiment, the method further comprises: connecting the cap to the guide.

In an embodiment, the method further comprises: connecting the funnel to the inlet.

In an embodiment, the inlet comprises a funnel support and a partly folded funnel connected to the funnel support by means of a clip, and the method further comprises the step of pushing the clip towards the guide.

Particular and preferred aspects of the invention are set out in the accompanying independent and dependent claims. Features from the dependent claims may be combined with features of the independent claims and with features of other dependent claims as appropriate and not merely as explicitly set out in the claims.

The above and other aspects of the invention will be apparent from and elucidated with reference to the embodiment(s) described hereinafter.

BRIEF DESCRIPTION OF THE DRAWINGS

FIG. 7 shows a top view of the element of FIG. 6 according to arrow VII.

FIG. 8 shows a bottom view of the element of FIG. 6 according to arrow VIII.

FIG. 9 shows a left side view of the element of FIG. 6 according to arrow IX.

FIG. 10 shows a right side view of the element of FIG. 6 according to arrow X.

FIG. 11 shows a cross-section of the element of FIG. 6 in the plane B-B.

FIG. 14a illustrates the liquid flow into the reservoir, and air flow out of the reservoir through the assembly when the movable element is in its first (lower) position.

FIG. 14b shows an enlarged view of a part of FIG. 14a.

FIG. 16a illustrates the blockage of liquid flow into and air flow out of the reservoir, and shows the passage of fluid from the inlet to the outlet by bypassing the movable element when it is in its second (upper) position.

FIG. 16b shows an enlarged view of a part of FIG. 16a.

FIG. 30 shows the funnel and the clip and part of the inlet of FIG. 20 in a first mounting position.

FIG. 31 shows the funnel and the clip and part of the inlet of FIG. 20 in a second mounting position.

Figure 1:
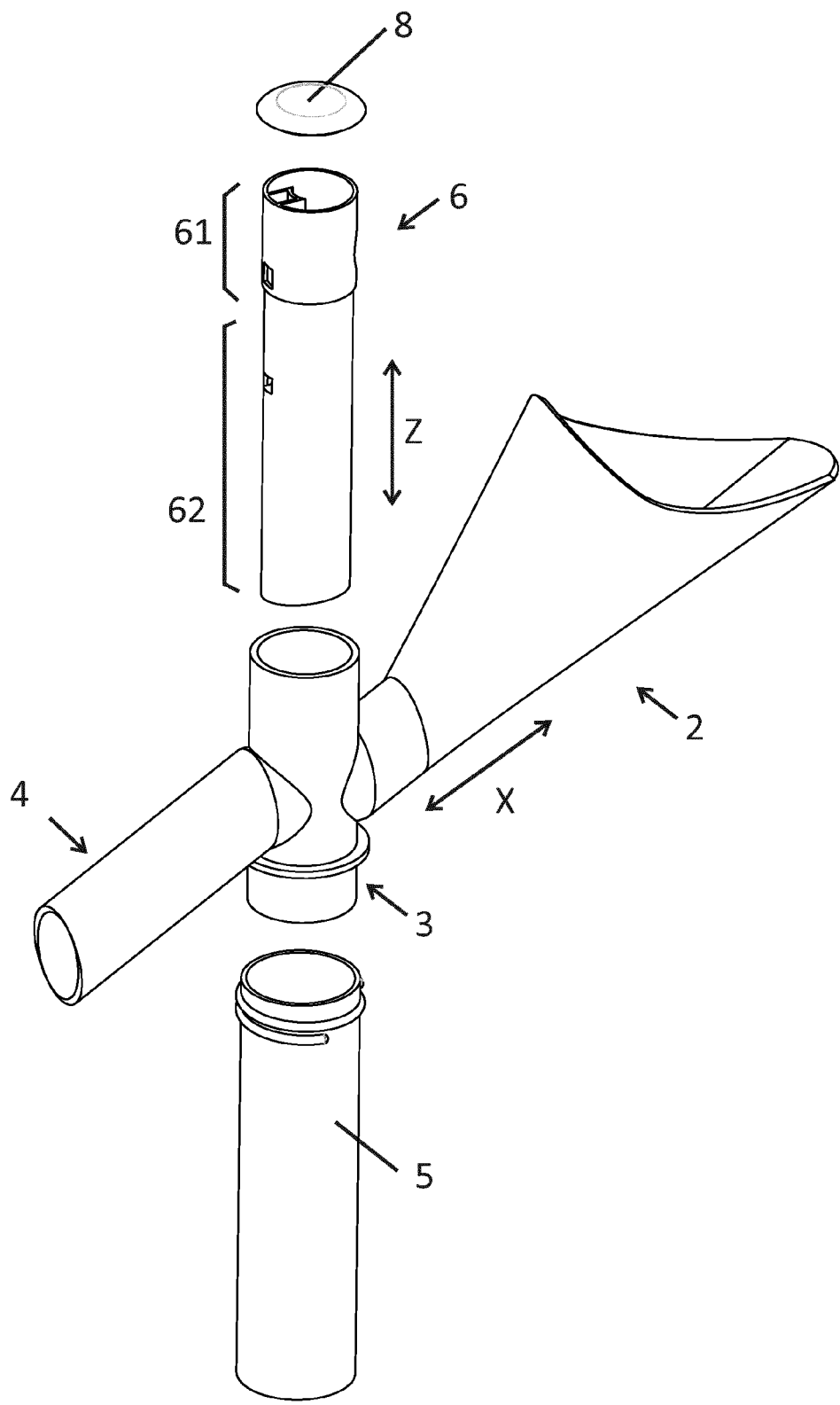
FIG. 1 shows an exploded view of a first embodiment of a device according to the present invention, comprising an assembly, a reservoir, a moveable element and a cap. The assembly comprises an inlet and an outlet coupled to a guide.
Figure 2:
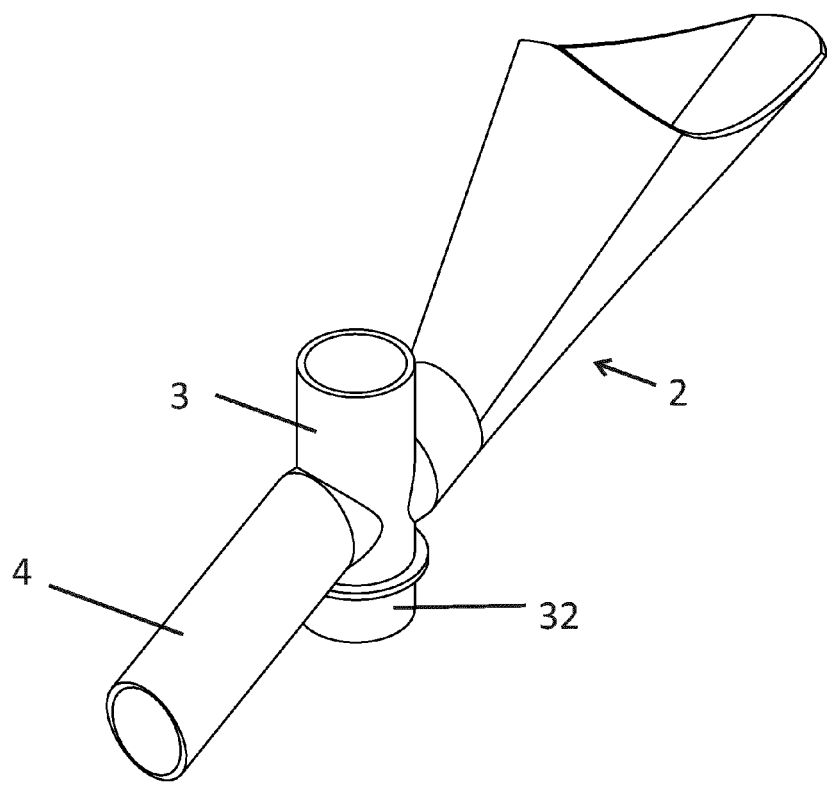
FIG. 2 shows the assembly of FIG. 1 in line drawings.
Figure 3:
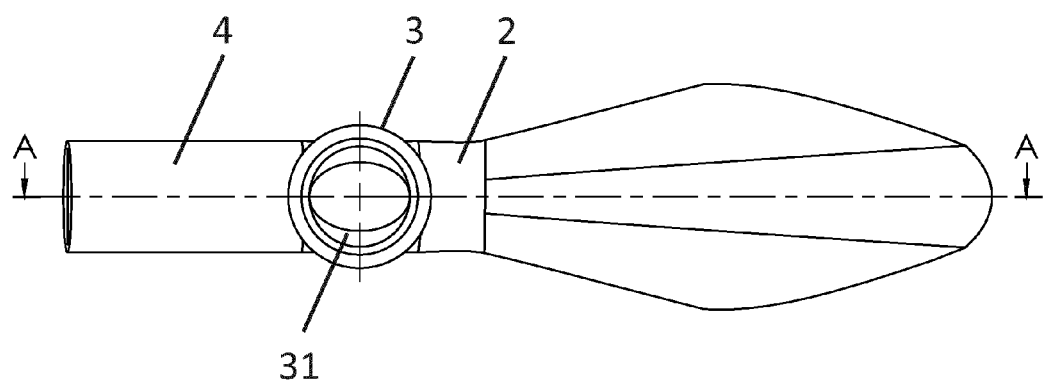
FIG. 3 shows a top view on the assembly of FIG. 2.
Figure 4:
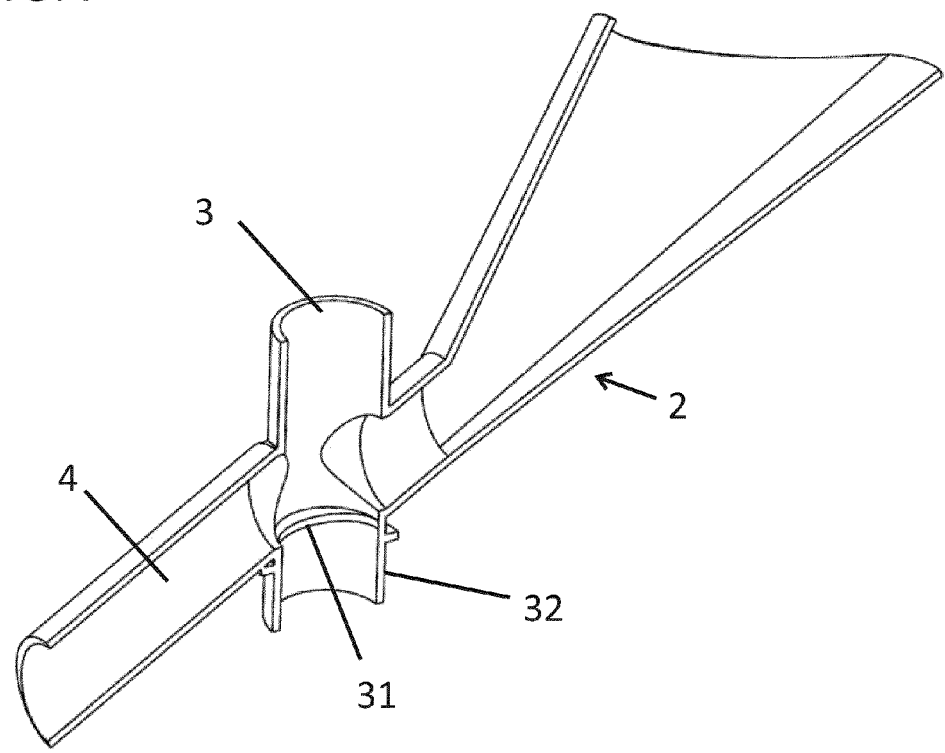
FIG. 4 shows a perspective sectional view of the assembly of FIG. 2.
Figure 5:
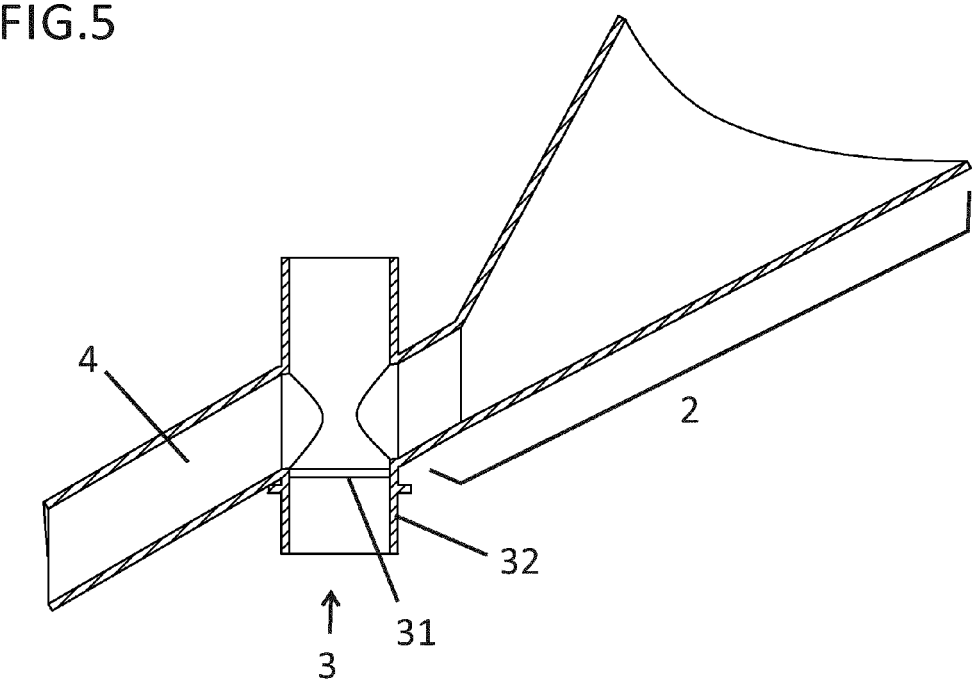
FIG. 5 shows a cross-sectional view of the assembly of FIG. 3 according to the line A-A.

The drawings are only schematic and are non-limiting. In the drawings, the size of some of the elements may be exaggerated and not drawn on scale for illustrative purposes.

Any reference signs in the claims shall not be construed as limiting the scope. In the different drawings, the same reference signs refer to the same or analogous elements.

DETAILED DESCRIPTION OF ILLUSTRATIVE EMBODIMENTS

The present invention will be described with respect to particular embodiments and with reference to certain drawings but the invention is not limited thereto but only by the claims. The drawings described are only schematic and are non-limiting. In the drawings, the size of some of the elements may be exaggerated and not drawn on scale for illustrative purposes. The dimensions and the relative dimensions do not correspond to actual reductions to practice of the invention.

The terms first, second and the like in the description and in the claims, are used for distinguishing between similar elements and not necessarily for describing a sequence, either temporally, spatially, in ranking or in any other manner. It is to be understood that the terms so used are interchangeable under appropriate circumstances and that the embodiments of the invention described herein are capable of operation in other sequences than described or illustrated herein.

Moreover, the terms top, under and the like in the description and the claims are used for descriptive purposes and not necessarily for describing relative positions. It is to be understood that the terms so used are interchangeable under appropriate circumstances and that the embodiments of the invention described herein are capable of operation in other orientations than described or illustrated herein.

It is to be noticed that the term "comprising", used in the claims, should not be interpreted as being restricted to the means listed thereafter; it does not exclude other elements or steps. It is thus to be interpreted as specifying the presence of the stated features, integers, steps or components as referred to, but does not preclude the presence or addition of one or more other features, integers, steps or components, or groups thereof. Thus, the scope of the expression "a device comprising means A and B" should not be limited to devices consisting only of components A and B. It means that with respect to the present invention, the only relevant components of the device are A and B.

Reference throughout this specification to "one embodiment" or "an embodiment" means that a particular feature, structure or characteristic described in connection with the embodiment is included in at least one embodiment of the present invention. Thus, appearances of the phrases "in one embodiment" or "in an embodiment" in various places throughout this specification are not necessarily all referring to the same embodiment, but may. Furthermore, the particular features, structures or characteristics may be combined in any suitable manner, as would be apparent to one of ordinary skill in the art from this disclosure, in one or more embodiments.

Similarly it should be appreciated that in the description of exemplary embodiments of the invention, various features of the invention are sometimes grouped together in a single embodiment, figure, or description thereof for the purpose of streamlining the disclosure and aiding in the understanding of one or more of the various inventive aspects. This method of disclosure, however, is not to be interpreted as reflecting an intention that the claimed invention requires more features than are expressly recited in each claim. Rather, as the following claims reflect, inventive aspects lie in less than all features of a single foregoing disclosed embodiment. Thus, the claims following the detailed description are hereby expressly incorporated into this detailed description, with each claim standing on its own as a separate embodiment of this invention.

Furthermore, while some embodiments described herein include some but not other features included in other embodiments, combinations of features of different embodiments are meant to be within the scope of the invention, and form different embodiments, as would be understood by those in the art. For example, in the following claims, any of the claimed embodiments can be used in any combination.

In the description provided herein, numerous specific details are set forth. However, it is understood that embodiments of the invention may be practiced without these specific details. In other instances, well-known methods, structures and techniques have not been shown in detail in order not to obscure an understanding of this description.

In the present disclosure, the terms "reservoir" and "recipient" are used as synonyms.

The present invention is about a device adapted to automatically capture a predetermined volume of one or more predetermined parts of a liquid stream, by secreting the liquid flow into at least two substantially disjoint parts, including for example, but not limited thereto, first void and mid-stream urine. If used for urine collection, the device can be used by both genders and can be used by children (if potty-trained) as well as adults and elderly. The device can be used in a sitting or a standing position. It can be conveniently held by the user to provide a liquid sample, e.g. a urine sample, in a collection funnel.

For capturing a first portion of a liquid stream, e.g. of a urine stream (known as "first void urine"), the device has a movable element ensuring a swift deviation of the liquid stream from the reservoir to the outlet tube as soon as the required volume is collected. The device can easily collect e.g. the first 1 ml to 15 ml of a liquid flow or urine, but the dimensions of the device can be varied to collect different volumes of liquid. The use of such a device according to embodiments of the present invention will enhance the reproducibility of sampling.

In case of urine collection, the device allows and ensures collection of first void urine, undiluted by mid-stream urine, and can be used for e.g. medical analysis. In alternative embodiments, the device also allows collection of mid-stream urine, uncontaminated by first void urine.

The device can for example be dimensioned for handling flow-rates ranging from less than 1 ml/sec to 55 ml/sec. For urine collection, 30 ml/sec is generally taken as the upper limit of a urine flow rate in a healthy individual. The flow rates that can be handled depend on the dimensions of the device according to embodiments of the present invention.

The device functions with or without interrupting the liquid flow, e.g. urine flow. There is no need to control the flow rate and if properly used no spillage of liquid or contamination of the environment will take place. It is user-friendly; for example in case of urine collection the person is allowed to urinate continuously without need for bladder control or taking the device out of the urine stream. The user can thus deliver his/her complete void urine fraction into the device at natural flow rate without user intervention other than appropriately holding the device. Limited manipulation by the user is required and there is no spillage and/or contamination of liquid or urine on the external surface of the device when used correctly. The device is therefore hygienic.

In settings where a predetermined amount of a liquid needs to be collected and mixed with a second substance already contained in the recipient (prefilled agent), a device according to embodiments of the present invention will simplify the sample taking and the mixing, and will avoid overfilling of the recipient and subsequent dilution of any prefilled agent. The prefilled agent, if present, may be a standard substance, or a component that may or may not be toxic and/or irritating. A device according to embodiments of the present invention will also avoid spillage of liquid to be sampled on the outside of the recipient, so it may be useful to collect in a safer and clean way potential toxic, infectious or unhygienic liquids such as e.g., but not limited thereto, urine, and, optionally, mix it with another potentially toxic substance, or obtain a potentially dangerous mix of substances in a safe and clean way. The fraction collected in the recipient will not be intermixed with nor diluted by the liquid that subsequently flows through the device.

A device according to embodiments of the present invention can be designed to allow the use of standard recipients for biological sample collection that may or may not contain DNA stabilization agents. If the recipient contains preservatives, the predefined portion of the liquid (e.g. first void) will be instantly in contact with the stabilization or chaotropic agents.

The device may find application in sampling of specific portions of urine, e.g. a first volume of the first void portion and/or a second volume of the mid-stream portion, but the device and technique are not limited to urine sampling.

FIG. 1 shows an exploded view of a first embodiment of a device 1 according to the present invention. The device 1 has a main part (shown in the middle) which may be an assembly of three separate parts: an inlet 2, an outlet 4 and a guide 3. The invention will be further explained as if the main part is an assembly of three separate parts, but the main part may also be a single monolithic part. The inlet 2 may comprise a tubular portion and a portion with the shape of a funnel where a fluid stream is to enter. A first portion of the fluid stream is to be captured by a reservoir 5, connected at a bottom side of the guide 3. An excess of the fluid stream will exit at the outlet 4. Also shown is an element 6 adapted for moving inside the guide 3, and a cap 8 for closing the guide 3, although the device 1 would also work without this cap 8.

FIGS. 2 to 5 show the main part in perspective view, top view, perspective sectional view and front view respectively. The guide 3 has a shape for holding the element 6, and has a cylindrical portion 32 underneath which serves to attach a reservoir 5. The cylindrical portion 32 may be adapted for attaching commercially available recipients, e.g. by push fitting or screw thread. The collection funnel in enclosed figures may be shaped to selectively collect urine from women and men. In an embodiment, the collection funnel is made of a relatively thin material optionally with pre-formed folding lines which can be reversibly folded (e.g. during production) and unfolded (e.g. by the end-user) or reversibly snap-compressed (e.g. during production) and decompressed (e.g. by the end-user) to reduce its volume, allowing the device including the funnel to be distributed to the end users by regular mail. Alternatively also preformed shapes can be used. Instead of the funnel shown in FIG. 2, other shapes or tubes for capturing liquid and leading it to the inlet 2 may also be used, such as e.g. a conical shape.

Figure 6:
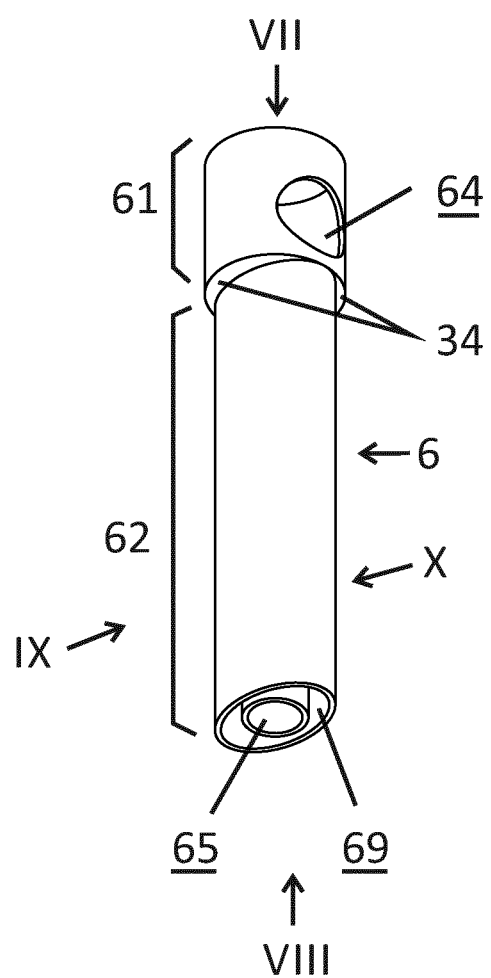
FIG. 6 shows a perspective view of the "movable element" shown in FIG. 1.

FIGS. 6 to 11 show the movable element 6 of FIG. 1 in more detail, and in several views. FIG. 6 shows the element 6 in perspective view. FIG. 7 shows a top view of the element of FIG. 6 according to arrow VII. FIG. 8 shows a bottom view of the element of FIG. 6 according to arrow VIII. FIG. 9 shows a side view of the element of FIG. 6 according to arrow IX. FIG. 10 shows a side view of the element of FIG. 6 according to arrow X. FIG. 11 shows a cross-section of the element of FIG. 6 in the plane B-B. The element 6 is to be placed in the guide 3 of the main part. In its first (lower) position in the guide 3, the lower edge 34 of the first segment 61, also referred to as "upper segment" of the element 6 rests on the elliptical inner edge 31 of the guide 3 (see FIG. 4).

The movable element 6 has several functions: a) it will serve as a pipe (referred to as "first channel") and initially lead the liquid stream into the attached container (recipient) 5 via a first internal channel 63, b) the pipe can be closed when the element 6 moves to its second (i.e. upper) position, c). The cross section of the first (upper) segment 61 of the element 6 in a plane perpendicular to its longitudinal axis is larger than the cross section of the second (lower) segment 62, for blocking passage from the inlet 2 to the outlet 4 when the element 6 is in its first (lower) position, so that the portion of the liquid flow is forced into the reservoir 5 through the pipe (first channel 63), and for allowing passage of the liquid flow from the inlet 2 to the outlet 4 when the element 6 is in its second (upper) position while blocking entrance into the pipe (first channel 63). The element 6 at least partly extends into the reservoir 5. In the example shown, the cross section of the upper part 61 is circular, while the cross-section of the lower part 62 is elliptical, but other shapes are also possible. A hydrodynamic shape, e.g. smooth shape, is preferred to reduce obstruction of the liquid flow from the inlet 2 to the outlet 4. The (elliptical) shape of the outer surface of the second (lower) part 62 is substantially complementary with the (e.g. elliptical) shape of the inner edge 31 of the guide 3, and the dimensions of the second segment 62, also referred to as "lower segment", are only slightly less than the dimensions of the inner edge 31, for allowing the element 6 to easily move upwards, while avoiding liquid to flow from the guide 3 into the reservoir 5 via the edge 31. The skilled person can find a suitable clearance by routine testing, or by trial and error. The inner edge 31 also enables easy insertion of the element 6 into the guide 3, and prevents the element 6 from falling (e.g. on the ground) when the reservoir 5 is removed (after capturing the predefined (e.g. first) liquid portion). Using a non-circular shape for the second (lower) segment 62 of the element 6 in combination with a substantially complementary inner edge 31 avoids rotation of the element 6 around its longitudinal axis, thereby ensuring that the first opening 64 (i.e. the entrance of the first channel 63 for receiving the liquid) and the fourth opening 68 (i.e. the air outlet of the second channel 65) remain well positioned respectively towards the inlet tube 2 and outlet tube 4. Using a non-symmetrical shape for the second lower segment 62 of the movable element 6 and a complementary shape for the edge 31 may prohibit incorrect assembly of the movable element 6 into the main element. Correct assembly may also be enforced by providing a rib (not shown) on the upper segment 61 of the movable part 6, adapted for gliding in a corresponding groove in the guide 3 of the main housing, or by providing a rib (not shown) on the upper part 3 of the main housing and a corresponding groove in the upper segment 61 of the movable element 6, or by using a flattened surface on one side of the cylinder. Other known techniques for preventing incorrect assembly may also be used.

The dimensions and weight of the movable element 6 and the dimensions of the reservoir 5 together determine the amount of liquid volume that will be collected. The skilled person can determine that amount, also referred to as predetermined volume. When the predefined amount of the first liquid portion, e.g. 1 to 15 ml for first void urine, has entered the reservoir 5, the element 6 will shift upwards (i.e. away from the reservoir 5) due to its lifting means 69. This will cause the first opening 64 to become blocked from the inlet 2 for avoiding further liquid to enter into the first channel 63, and thus into the reservoir 5. At the same time a bypass channel is created inside the guide 3, from the inlet 2 to the outlet 4, next to the element 6, because of the smaller cross-section of the second (lower) segment 62 (e.g. a smaller transverse diameter in case of an elliptical shape) than the cross-section of the first segment 61, and thus of the corresponding inner cross section of the guide 3.

Element 6 also comprises a second channel 66, formed between a third and fourth opening 67, 68, which is used for evacuating air from the reservoir 5 when filling the reservoir 5 with the predefined (e.g. first) liquid portion. Although FIG. 9 shows square openings 67, 68, other shapes are also possible, e.g. circular openings, or elongated openings, e.g. rectangular openings or elliptical openings. This allows smooth filling of the recipient 5, i.e. easy and fast filling without jerks. This works as follows (see also FIG. 14*a* and FIG. 14*b*). When the reservoir 5 is empty, and the element 6 is in its first (lower) position, the third opening 67 is in gas/air connection with the reservoir 5, and the fourth opening 68 is in gas/air connection with the outlet 4, so that air can escape from the reservoir 5 into the outlet 4 via the third opening 67 and the second channel 66 and the fourth opening 68, when liquid enters the reservoir 5. When the predefined amount of the predefined (e.g. first) portion of the liquid flow has entered the reservoir 5, and the element 6 has moved to its second (upper) position, the third and the fourth opening 67, 68 are closed by wall sections of the guide 3 (see also FIG. 16*a* and FIG. 16*b*), for preventing liquid, in particular a subsequent portion of the void, to enter the reservoir 5 via the second channel 66 (also referred to as the "air channel").

As mentioned, the element 6 has lifting means for moving the element 6 upwards when the first liquid portion has entered the reservoir 5. The lifting means may be adapted for floating on liquid already collected, thereby moving upwards when liquid enters the reservoir 5. In the embodiment shown in FIGS. 6-11, the element 6 has one or more air chambers 69 (i.e. compartments open at their lower end, but closed at their top). By choosing appropriate dimensions, and depending on the weight of the element 6, these one or more air chambers 69 will cause the element 6 to move upwards, due to the Archimedes force, when the element 6 is at least partly submerged in the liquid in the reservoir 5. Another way to provide sufficient floating capacity to element 6 without using one or more air-chambers 69, may be to cover the element 6 by a material having a mass density lower than the liquid to be captured (optionally mixed with an agent, as described above), e.g. Styrofoam® in case of urine collection. Styrofoam is a trademark of a closed-cell extruded polystyrene foam, but other foam material may also be used, provided it has a mass density lower than that of the liquid.

In the embodiment of FIGS. 6-11, the guide 3 has an open top, which can be closed by a cap or lid 8 for avoiding contamination of the liquid sample, as well as ensuring proper use of the device 1 (e.g. avoiding spillage).

The reservoir (or recipient) 5 serves to capture, store and transport the first (or later) portion of a predefined amount of a liquid stream. It can be attached to the guide 3, e.g. to a cylindrical portion thereof, by threaded engagement, friction fit or other engagement easy to disrupt. In an embodiment, this reservoir 5 is partly prefilled with a substance to be mixed with the liquid to be collected. For example, if the device 1 is used to capture first void urine for DNA based testing, it is recommended to add a DNA stabilization agent prior to collecting the urine. A volume ranging from 1 to 15 ml is very suitable for capturing first void urine for DNA based STI testing. After use, the reservoir 5 can be detached from the guide 3, and should be closed by a proper cap or lid for transport, storage, and analysis without spillage or contamination. Such reservoirs 5 are commercially available.

Suitable materials for the device are: polypropylene, paper or biodegradable polymers such as the bioplastic Plantic®, commercially available from the company Plantic Technologies Limited (UK), but other materials could be used as well. The material should be able to withstand fluid at ambient temperature or body temperature for urine collecting purpose (i.e. about 15° to 40°, such as for example 35 to 40° C.) and keep the device 1 in shape for the duration of the liquid collection (e.g. at least 5 minutes). The material should not have physic-chemical effects on the sampled fluid, e.g. urine, and not contaminate the liquid, e.g. urine, or affect medical analysis. In case of biodegradable polymer, the material may provide an advantage by being readily flushable after use.

Figure 12:
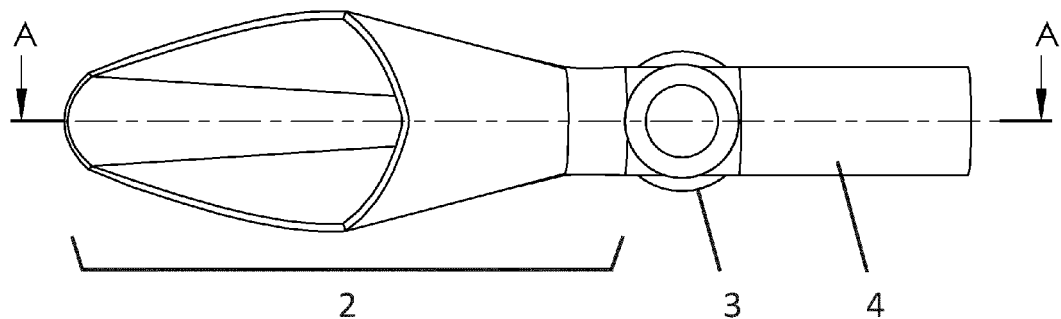
FIG. 12 shows a top view of the assembly of FIG. 3 further comprising a cap.
Figure 13:
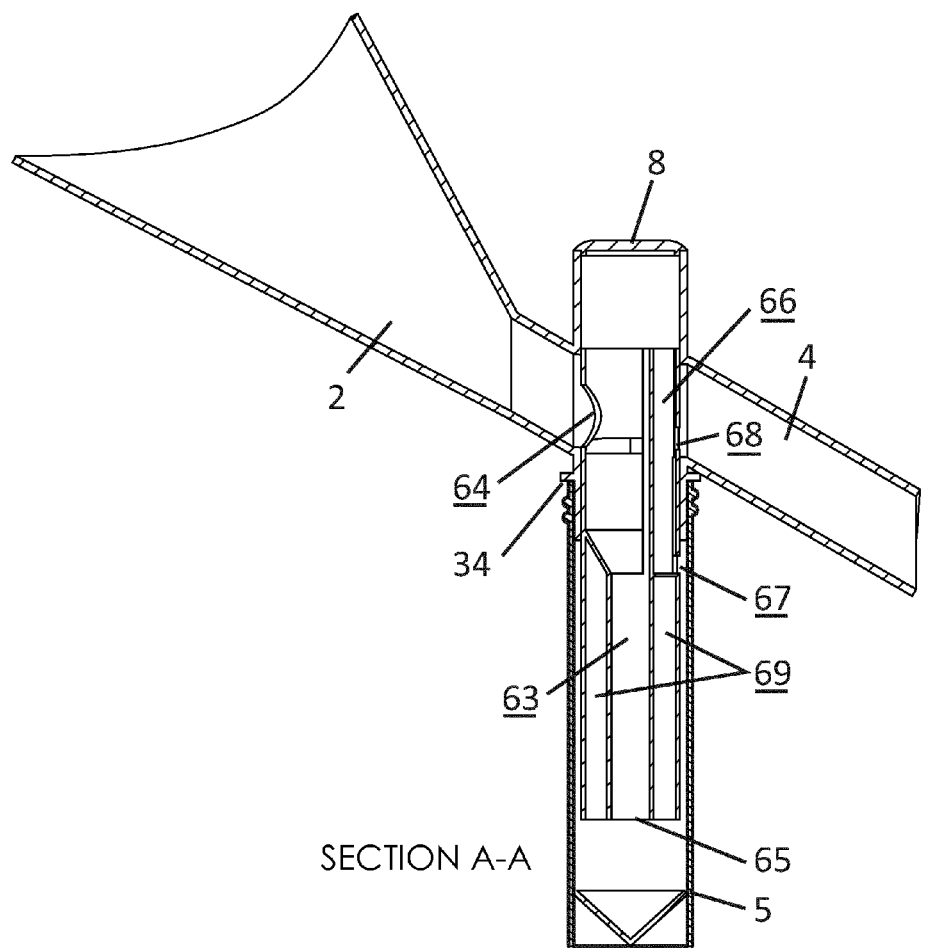
FIG. 13 shows a cross-section of the assembly of FIG. 12 with the movable element located in the first (lower) position for directing the first portion of the liquid flow into the reservoir.

Referring to FIG. 1 and to FIG. 12 and FIG. 13, the device 1 can be produced and assembled as follows. The main component, comprising the inlet 2, the guide 3, and the outlet 4 as well as the movable element 6 can be produced by injection moulding. The main component can be moulded as separate parts (i.e. the guide 3, the inlet 2, the outlet 4) and assembled (i.e. by push fitting) or can be produced by injection moulding as a single part. To assemble the device 1 the element 6 can be inserted in the guide 3 from the top. The element 6 should be oriented in such a way that the first opening 64 is oriented towards the inlet tube 2. Optionally the second (lower) segment 62 can be made asymmetrical for avoiding misplacement, e.g. the second segment may have a side rib (not shown), and the edge 31 of the guide 3 may have a corresponding notch (not shown). In particular embodiments of the present invention, the top of the guide 3 may be sealed by a cap 8. A reservoir 5 can be attached to a cylindrical portion 32 (FIG. 4) of the guide 3, e.g. by push fitting, or by screw thread, or in any other way known in the art. Optionally an indication, such as e.g. a colour or note may be applied to a portion of the element 6, e.g. between the lower edge 34 of the upper segment and the third opening 67 to allow the user to visually check if the movable part 6 is in its correct position prior to use of the device 1. Assembly may take place at a fixed place (e.g. production plant) or may be done locally by e.g. the end user.

In an embodiment, the device 1 can be dimensioned and constructed in such a way that it or its components can be stored in a relatively flat box having dimensions smaller than e.g. 380 mm×265 mm×32 mm, so that it or its components may be shipped by regular mail. Such a box would fit into a "standard" letter box, the exact dimensions of which may slightly deviate per country. Such dimensions allow the device to be shipped via a standard mailbox, allowing for self-sampling at home and delivery of the device 1, or its disassembled parts, and at the same time, or subsequently also the reservoir 5 with the liquid sample by mail. In an embodiment, parts of the device 1, in particular the funnel may be compressed or folded, e.g. by using a snap operation. Of course, before use, the device 1 should be unfolded and/or expanded and/or assembled, so that the device 1 retains its intended shape for optimal liquid collection.

The device 1 can be used to capture a pre-determined volume of a predefined portion of a liquid stream. The volume to be captured is related to the dimensions and weight of the different parts, which dimensions and weight can be adapted in function of the required sampling specifications. If desired, the reservoir 5 may be prefilled with a reagent to be mixed with the liquid upon sampling. The reagent may be a solid material, or a fluid material.

To explain in detail how the device 1 will function, it is assumed that the device is used for the collection of first void urine, and that the reservoir 5 already contains a DNA preservation buffer, and that the components of device 1 are packed in a box or letter, and delivered by regular mail. First step is to unpack the box or letter. Next step is to insert the element 6 into the guide 3, to close the guide 3 by the cap 8, and to unfold the funnel in case it was folded, and in case the guide 3 and the inlet 2 and/or the outlet 4 are separate parts, to connect the inlet 2 and/or the outlet 4 to the guide 3. Optionally an indication, such as e.g. a colour or note may be applied to a portion of the element 6, e.g. between the lower edge 34 of the upper segment and the third opening 67 to allow the user to visually check if the movable part 6 is in its correct position prior to use of the device. Of course, if the device 1 was entirely or partly pre-assembled, some or all of the above assembly steps can be omitted.

Figure 15:
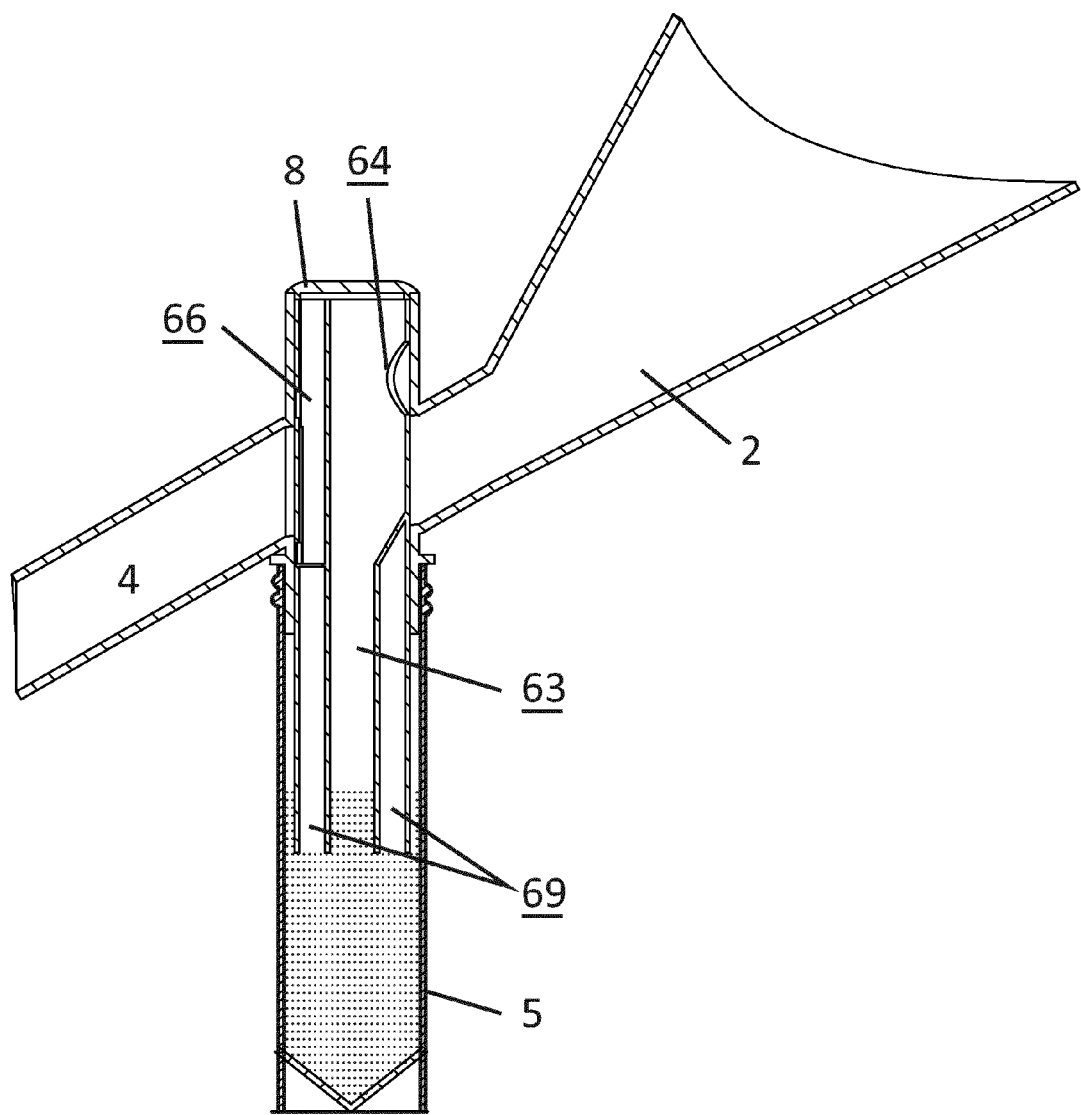
FIG. 15 shows a cross-section of the assembly of FIG. 12 with the movable element located in the second (upper) position for directing the second portion of the liquid flow to the outlet.

Next step is to open the reservoir 5 while keeping it upright to avoid spillage, and to attach it to the guide 3 (or the main component). This may e.g. be done by sliding or by screwing. Then the person holds the device 1 so that his or her urine will enter the funnel, and that the outlet 4 is directed into the toilet. A liquid sample can then be taken in a standing or sitting position. The funnel may have a design suitable for both genders. When the person starts urinating the element 6 will be initially located in its first (lower) position (FIG. 13). The urine flowing in the funnel will flow via the inlet tube 2 into the first opening 64 of the element 6, and through the first channel 63, and will end substantially at the bottom of the reservoir 5, where the urine will immediately mix with the conservation liquid, if present. Due to the second channel 66 (also called "the air channel") no substantial counter pressure to the liquid column will build up in the reservoir 5. Excess air will escape via the air channel 66 into the outlet 4. Since the fourth opening 68 is in communication with the outlet 4, the escaping air will not interfere (e.g. hinder) the entrance of the liquid into the reservoir 5, which is advantageous as compared to some prior art systems. In FIG. 14a and FIG. 14b, the liquid flow is indicated in solid line, the air-flow is indicated in dotted line. When the liquid level in the reservoir 5 reaches the bottom end of the element 6, air in the air chamber 69 is trapped, and the one or more air chambers 69 will function as lifting means for moving the element 6 upwards, i.e. towards its second position. The lifting means provide floating capacity to the element 6, so as to move it upwards as the reservoir gets filled. As more liquid is entering the reservoir 5, the element 6 starts to move upwards, while air is being evacuated via the second channel 66 (see also FIG. 15). The amount of liquid to be captured is primarily controlled by the dimensions of the reservoir 5. However, in order to ensure that the element 6 is lifted when the predefined amount of liquid is present in the reservoir, the element 6 should have sufficient floating capacity to overcome its weight and a static friction force between the element 6 and the guide 3, in particular between the second segment 62 and the inner edge 31 of the guide 3. The floating capacity can be increased by increasing the volume of the air chamber(s) 69, or by adding material having a mass density lower than that of the liquid to be captured, such as e.g. Styrofoam®. By the time the predefined amount of liquid has flown in the reservoir 5, the element 6 has reached its second (upper) position, and the first opening 64 has shifted behind a wall section of the guide 3, so that the first channel 63 is decoupled from the inlet 2, and the third and fourth openings 67, 68 have shifted against a wall section such that the second channel 66 is decoupled from the outlet 4. A very advantageous characteristic of this embodiment is the fact that, during the capturing of the first liquid portion, the inlet flow is not hampered by any obstacles (including air pressure) upon which the flow would exert a downward directed force, which would prevent the element 6 from moving upwards. In other words, the downward force component exerted on the element 6 is negligible. Also the air flow escaping from the reservoir 5 when liquid enters the reservoir 5 is not interfering with the incoming liquid stream through the first channel 63, because air escapes via a different channel 66. This allows the first liquid portion to enter the reservoir 5 more rapidly. In this way, mixing of the first liquid portion with a subsequent liquid portion because of a limited streaming capacity e.g. due to internal flow friction is avoided. It is a major advantage of this mechanism that it is capable of sampling the predetermined amount of liquid substantially independent of the liquid flow rate, which may be constant, or may vary between relatively wide ranges. Tests using a prototype dimensioned for urine collection have shown good performance at flow rates from less than 1 ml/sec up to 55 ml/sec, the latter being more than twice the maximum flow in healthy individuals, which is about 30 ml/sec. The prototype still works correctly, even when tilted such that the elongated element 6 makes an angle of 15° with the vertical direction. In contrast, in the device described in WO2004010873, the flow rate is limited at several locations in the device (in particular in the valve inlet, shut-off chamber, and the valve outlet), and that flow rate is decisive for which part of the liquid will be captured, and which part of the liquid will overflow. Moreover, in the prior art device, mixing between the first and second liquid portion is not completely eliminated, as long as the reservoir is not closed. Furthermore, the closure is based on surface tension, which is less reliable and less predictable than mechanical blockage as used in the present invention. Indeed, from the moment that the element 6 starts moving upwards, a passage is created inside the guide 3 from the inlet tube 2 to the outlet tube 4, in the form of a bypass channel, formed between the second (lower) segment 62 of the element 6 and the inner surface of the guide 3, as indicated by the dotted line in FIG. 16a and FIG. 16b, taking into account the smaller cross-section (e.g. smaller diameter) of the second segment 62. As can be seen from the same figures, when the element 6 has moved up to its second (upper) position, the first opening 64 is closed, thereby avoiding entrance of liquid into the first channel 63, and thus from the inlet 2 to the reservoir 5, and also the third and fourth opening 67, 68 are closed, thus the second (air) channel 66 is closed, thereby avoiding any liquid to flow into the reservoir 5 via the outlet 4 when the element 6 is its upper position, that is, when the first liquid portion is captured. So further filling of the reservoir 5 via any of the two different routes (i.e. first channel 63 or second channel 66) is avoided. No further liquid can enter the reservoir 5. In addition, the person providing the liquid sample does not need to control his/her bladder so as to control the liquid flow rate, in particular, he/she does not have to interrupt his/her urine flow and can simply continue urinating until finished. The next step is to remove the reservoir 5 from the guide 3 (or from the main component in case of a single part). By doing so, the element 6 will be removed from the reservoir 5, and the liquid level in the reservoir 5 will drop because of removal of element 6. Thanks to this level drop, the risk of spilling liquid when detaching the reservoir 5, or when closing the reservoir 5 is drastically reduced. The reservoir 5 containing the sample of first void urine can then be closed by a cap or lid to prevent contamination and or spillage during transport or storage. The closed reservoir 5 can then be shipped, e.g. to a lab for e.g. medical analysis. Alternatively, readout means, such as e.g. a colour code on a test strip, may be provided on the device, placed so as to be in contact with collected liquid, for allowing the user to read out a test result.

Figure 17:
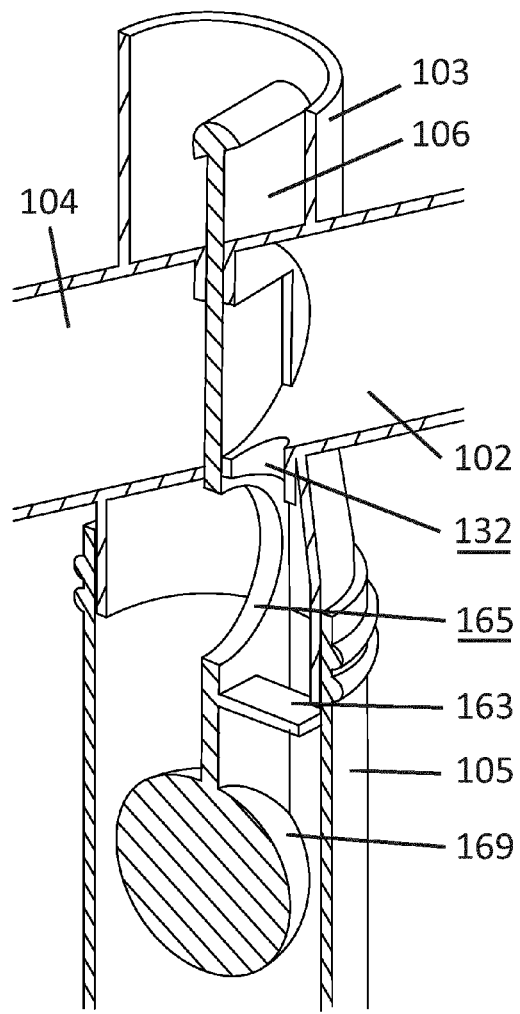
FIG. 17 shows an example of a guide and element (of which the front half is removed), according to a second embodiment of a device according to the present invention, in perspective view, the element being located in the first (lower) position for capturing liquid in the reservoir.
Figure 18:
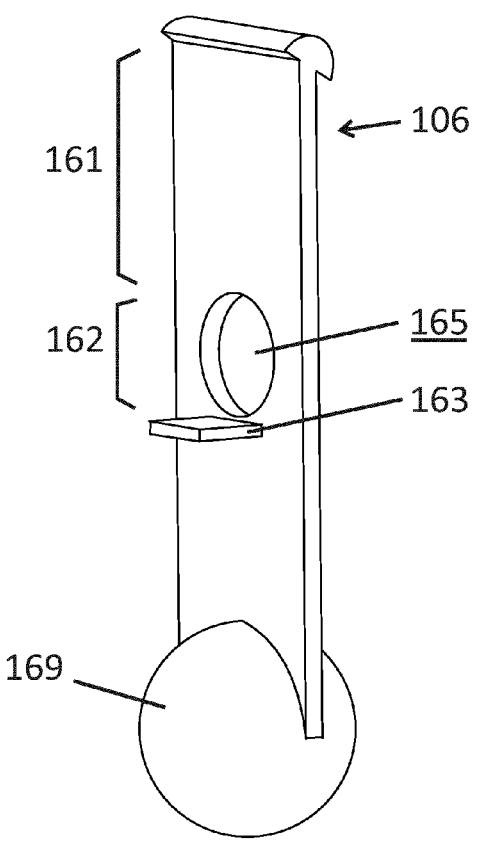
FIG. 18 shows the element of FIG. 17 in its entirety.

Although the working principles are described above for only one embodiment of the device, other embodiments of the device can also be used. A second embodiment of the device 101 is shown in FIG. 17 and FIG. 18. FIG. 17 shows an example of a guide 103 and a corresponding movable element 106 (of which the front half is removed), in perspective view. The element 106 is located in the first (lower) position for capturing liquid in the reservoir 105 (not shown). FIG. 18 shows the element 106 in more detail. The device 101 functions in largely the same way as the device 1 of the first embodiment, but there are some differences. For example, the guide 103 has a first opening 132 arranged between the inlet 102 and the reservoir 105, and the element 106 has a protrusion 163 adapted for blocking the first opening 132 when the element 106 is in its second (i.e. upper) position, while leaving the first opening 132 open when the element 6 is in its first (i.e. lower) position for receiving the first fluid portion. The element 106 has a first (upper) segment 161 with a closed wall section and a second (lower) segment 162 with a narrowing (not illustrated in the drawings, but could have the shape of a guitar body) or with a second opening 165 arranged such that the closed wall section blocks passage from the inlet 102 to the outlet 104 when the element 106 is in the first (lower) position for directing the first fluid portion towards the reservoir 105, while allowing passage of the second fluid portion from the inlet 102 to the outlet 104 when the element 106 is in the second (i.e. upper) position. In this embodiment no air chamber is used as lifting means, but instead an object, e.g. a spherical or hemi-spherical object 169 made of a material with a mass density lower than that of the liquid to be captured, is mounted to the element 106. Apart from this object 169, the first (upper) segment 161 and the second (lower) segment 162 of the element 106 may be substantially planar. This offers the advantage that it is easy to produce, and requires less material.

Figure 19:
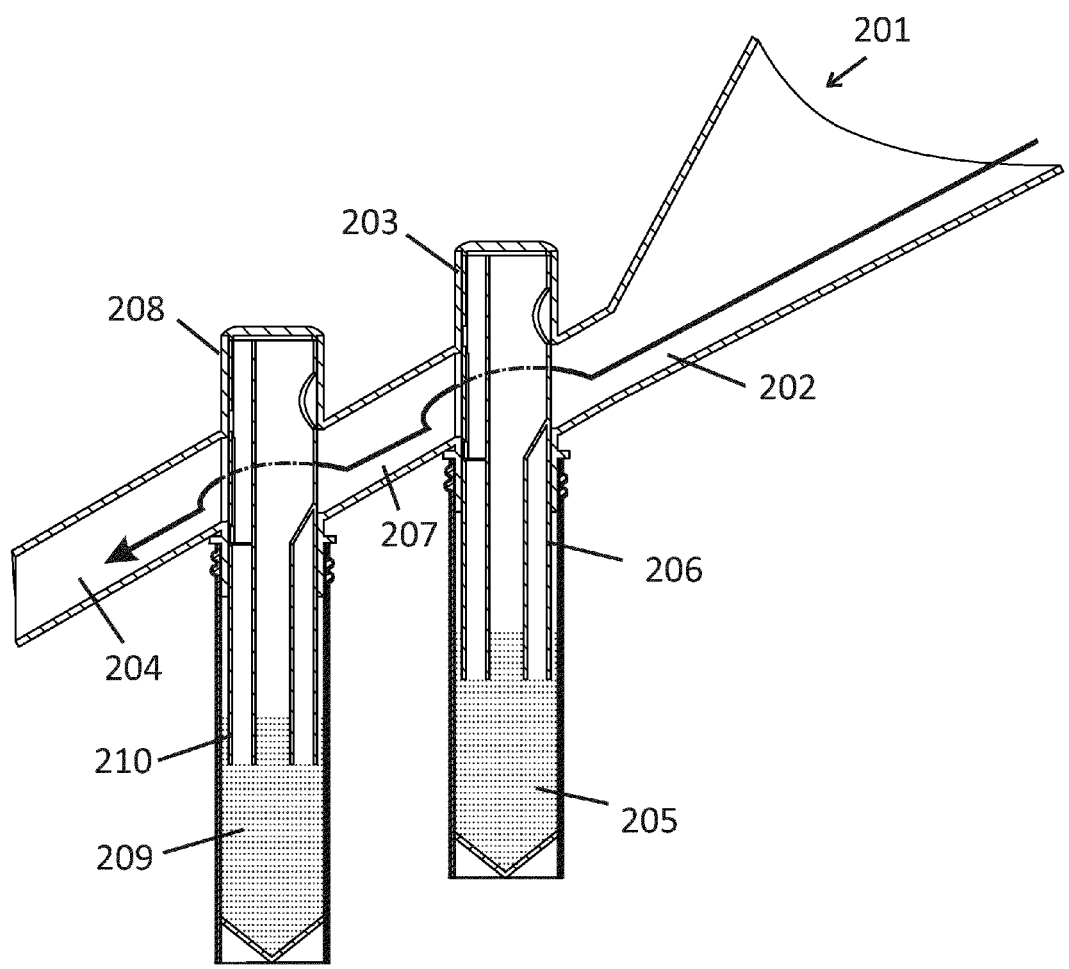
FIG. 19 shows a device for capturing a first portion of the liquid flow in a first reservoir, and for capturing a second portion of the liquid flow in a second reservoir, and for passing an excess of the liquid flow to the outlet, according to a third embodiment of a device according to the present invention.

FIG. 19 shows a third embodiment of a device according to the present invention. FIG. 19 shows a device 201 for capturing a first portion of the liquid flow in a first reservoir 205, and for capturing a second portion of the liquid flow in a second reservoir 209, and for passing an excess of the liquid to the outlet 204. The device 201 may comprise an inlet 202, a first guide 203, a tubular interconnection 207, a second guide 208, and an outlet 204. These parts may be individual parts to be assembled, or may be provided as a single monolithic part. The first reservoir 205 would be connected to the first guide 203, the second reservoir 209 would be connected to the second guide 208. The first guide 203 would have a first element 206 movable therein, and the second guide 208 would have a second element 210 movable therein. Optionally a first cap is provided for closing the first guide 203, and a second cap is provided for closing the second guide 208. The first guide 203 may be identical (e.g. in shape and/or dimensions) to the second guide 208, but may also be different. The first reservoir 205 may be identical (e.g. in shape and/or dimensions) to the second reservoir 209, or may be different. By using different reservoirs 206, 209, the risk of confusing which reservoir contains the first liquid portion resp. the second liquid portion, is eliminated.

Such a device 201 would be ideally suited for capturing a first portion of a liquid flow, e.g. the first void urine, in the first reservoir 205, and a second portion of the liquid flow, e.g. midstream urine, in the second reservoir 209. Of course, this device 201 can also be used for capturing only a second urine void, whereby the first urine void is disposed of, after capturing.

FIG. 20 to FIG. 31 illustrate a fourth embodiment of a device according to the present invention. The device 301 looks and functions very similar to the device 1 of the first embodiment described above, except where explicitly mentioned. Therefore, most of what has been described above is also applicable for this fourth embodiment, unless stated otherwise.

Figure 20:
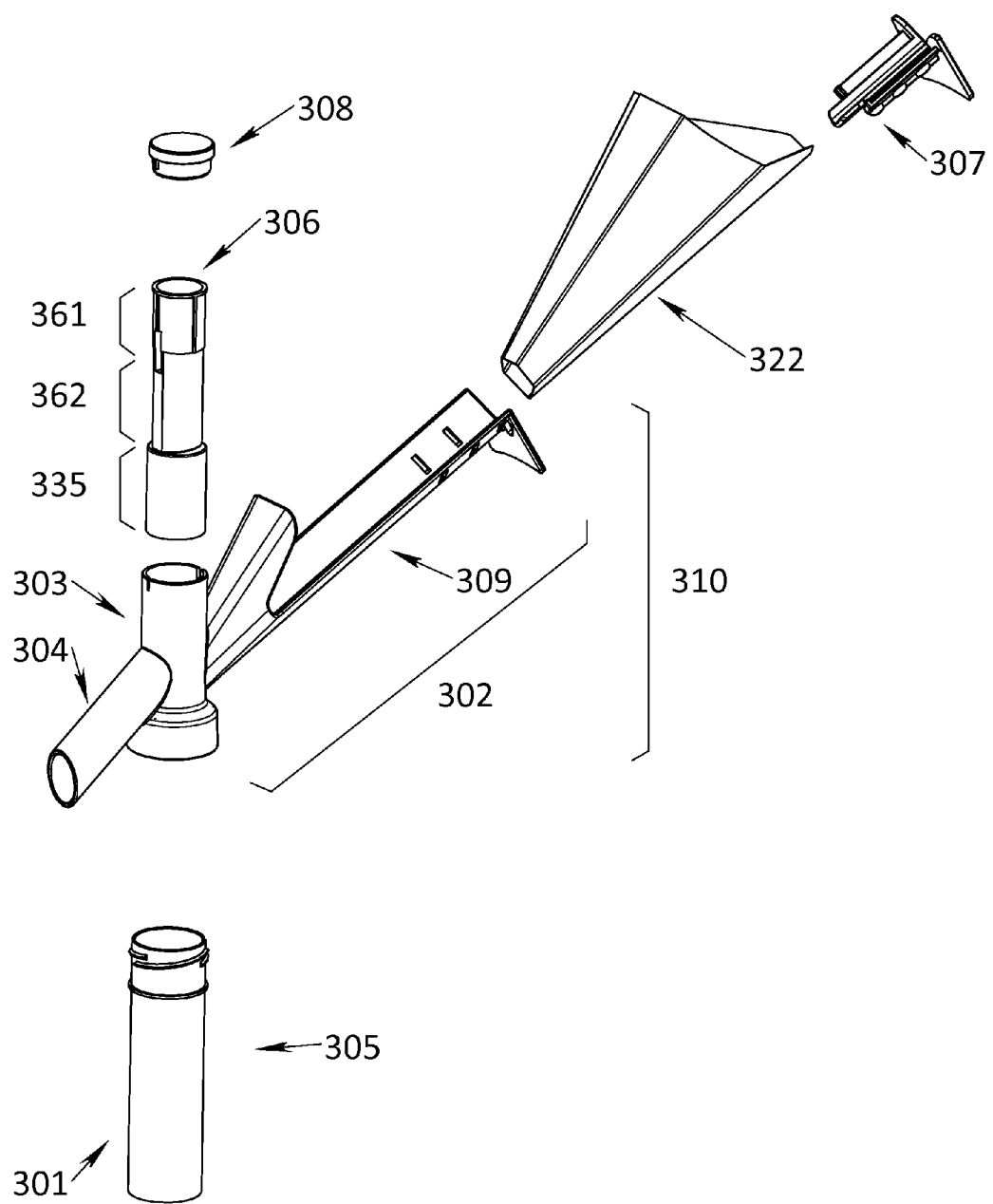
FIG. 20 shows an exploded view of a fourth embodiment of a device according to the present invention, comprising an assembly having a guide with an inlet and an outlet, and a movable element comprising three segments. The inlet comprises a funnel support and a separate funnel, and a clip.

FIG. 20 shows an exploded view of the device 301. It comprises a main housing 310 which may be a monolithic part or an assembly of three separate parts: a guide 303, an inlet 302 and an outlet 304. In what follows, the terms "main housing" 310 and "assembly" are used to indicate the same.

The inlet 302 may comprise a portion, referred to as funnel support 309 adapted for receiving a separate funnel part 322. The funnel support 309 may be a slender portion having a particular shape, such as e.g. a conical shape with at at least one elongated portion having a U-shape or V-shape. The funnel support 309 may have one or more slots for engagement with a clip 307, as will be described further. The clip 307 can also be used for other purposes, e.g. for keeping the funnel 322 in an open (unfolded) position when it was at least partly folded (e.g. substantially closed) for transport, and/or for keeping the device 301 in an upright position when placed on a horizontal surface before or after urine sampling.

The funnel 322 of this embodiment may be made of carton, paperboard or cardboard, optionally coated with a liquid-tight coating or liquid-repelling coating, e.g. varnish. The funnel 322 may be folded or compressed (fully or partially) for easy transport, and can be unfolded or uncompressed by the end-user. The clip 307, mountable on the funnel support 309, can be used for mounting the funnel 322 to the inlet 302 and/or for maintaining the funnel 322 in its unfolded shape during actual use of the device 301. This clip 307 may also be used as a support for stably positioning the device 301 after use.

The device 301 further comprises a movable element 306, which is movable in the guide 303 between a first position wherein a first portion of the liquid flow is directed towards the reservoir 305, and a second position wherein the remainder of the liquid flow is directed towards the outlet 304. The movable element 306 of this embodiment comprises three segments, referred to as the first segment 361, second segment 362, and a third segment 335. Whereas the movable element 6 of the first embodiment (FIG. 1) consists of a single component, the movable element 306 of the fourth embodiment may consist of two separate parts which are assembled together: a first part comprising the first and second segment 361, 362, and a second part comprising the third segment 335.

The device 301 further comprises a reservoir 305, which may have an external screw thread, for engaging with an internal screw thread of the guide 303.

The device 301 may optionally further comprise a cap 308 for closing the guide 303, although this is not necessary for functioning correctly.

Figure 22:
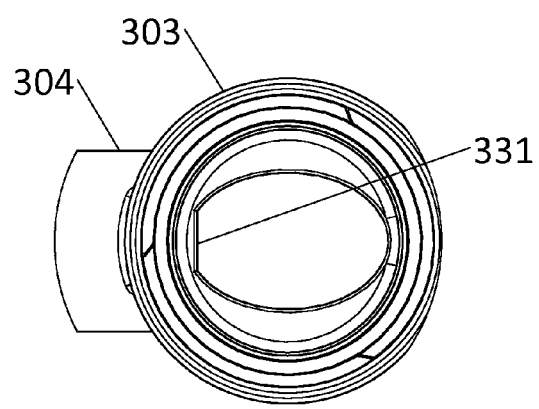
FIG. 22 shows part of the assembly of FIG. 21 in enlarged view.
Figure 23:
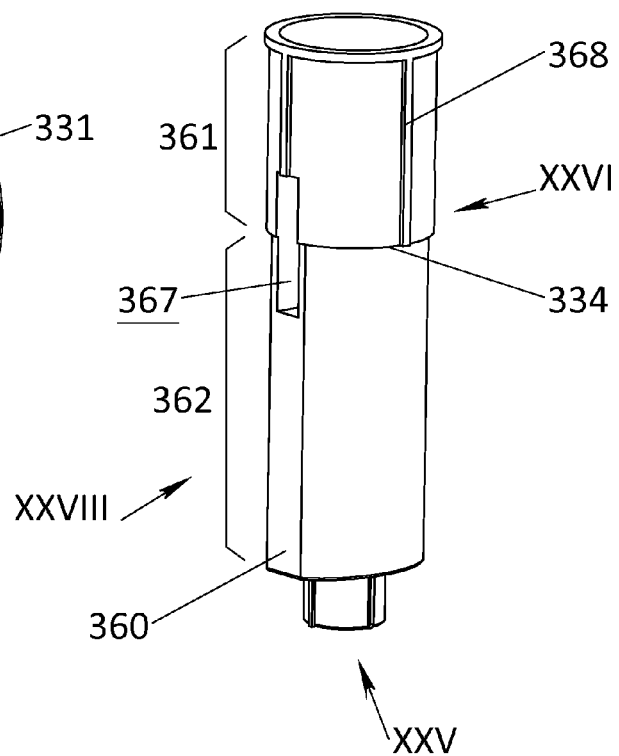
FIG. 23 shows the first and second segment of the movable element of FIG. 20 in enlarged perspective view.

The device 301 can be produced and assembled as follows. The main component 310, comprising: the inlet 302, the guide 303, and the outlet 304; as well as the other elements: the funnel 322, the movable element 306, the clip 307, the cap 308 and the funnel support 309 can be produced e.g. by injection moulding. The main component 310 can be moulded as separate parts (i.e. the guide 303, the inlet 302, the outlet 304) and assembled (e.g. by push fitting) or can be produced by injection moulding as a single part. To assemble the device 301 a first part of the element 306 comprising the first and second segment 361, 362 can be inserted in the guide 303 from the top. The element 306 should be oriented in such a way that the substantially linear inner edge portion 331 of the guide 303 faces the substantially planar surface portion 360 of the second segment 362 (FIGS. 22 and 23). This ensures proper orientation of the movable element 306 into the guide 303, in particular that the opening 304 (FIG. 26) is directed towards the inlet 302. The third segment 335 can then be inserted from the bottom of the guide 303 and be assembled to the first part of the element 306 e.g. by push fitting. The air chamber 369 formed in the third segment 335 should be faced downwards. Although not necessary for the proper functioning of the device 301, the top of the guide 303 may be sealed by a cap 308. The funnel 322 can be supported and shaped by funnel support 309. Clip 307 can hold the funnel 322 in place for transportation purposes and during actual use. A reservoir 305 can be attached to the main housing 310 by means of screw thread 351, or in any other way known in the art.

Figure 21:
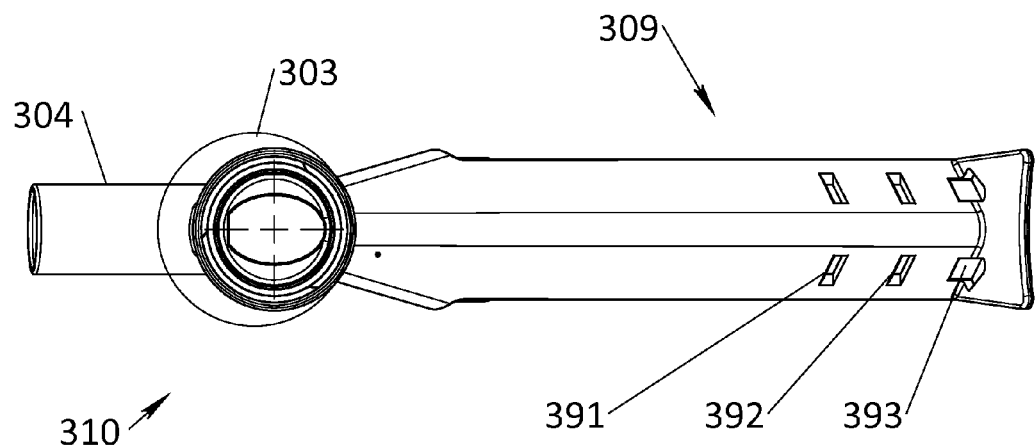
FIG. 21 shows the assembly of FIG. 20 in top view.

FIG. 21 shows the main part 310 of FIG. 20 in top view. The funnel support 309 and the clip 307 may comprise cooperating engagement means, such as e.g. openings 391, 392 in the funnel support 309 for receiving protrusions, such as e.g. clip snaps 371 of the clip 307, but other known engagement means may also be used. This engagement will be further described in relation to FIG. 29 to FIG. 31.

FIG. 22 shows part of the assembly of FIG. 21 in enlarged view. Visible is a substantially elliptical opening for receiving the second segment 362 of the movable element 306, but the opening has a linear portion, corresponding to a flat surface of the movable element 306, for preventing the element to be inserted incorrectly in the guide 303.

FIG. 23 shows the first and second segments 361, 362 of the movable element 306 of FIG. 20 in enlarged perspective view. The first segment 361 may be substantially cylindrical with zero or more longitudinal ribs 368. Providing such ribs may reduce the friction between the movable element 306 and an inner wall of the guide 303.

When comparing FIG. 23 with FIG. 1 or FIG. 9 it can be seen that the two openings 67, 68 are replaced by a single trench 367, offering the same functionality, that is: providing an air channel between the reservoir 305 and the outlet 304 when the element 306 is in its first (lower) position, and blocking said air channel when the element 306 is in its second (upper) position.

Figure 24:
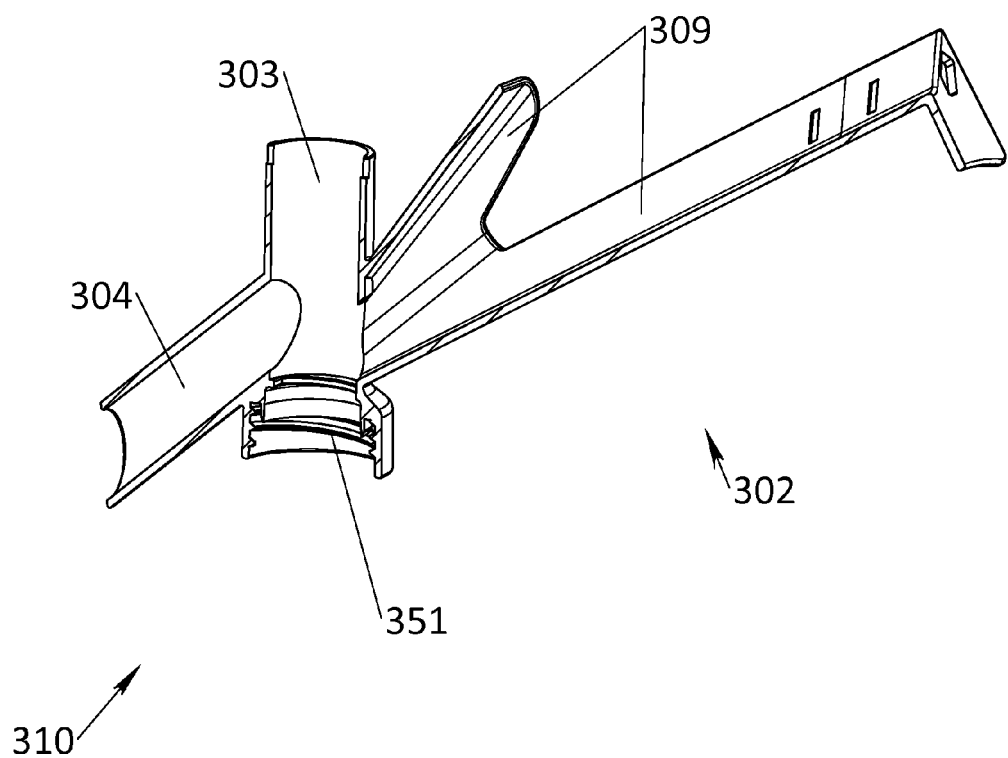
FIG. 24 shows the assembly of FIG. 20 in perspective view, the front half of the assembly being removed for illustrative purposes.

FIG. 24 shows the assembly 310 of FIG. 20 and FIG. 21 in perspective view, but the front half of the assembly is removed for illustrative purposes. This figure shows that a lower portion of the guide 303 may have an internal screw thread 351 for connection with a reservoir 305 having an external screw thread. As mentioned before however, such screw thread is not absolutely necessary, and the reservoir 305 may also be fitted in other ways. FIG. 24 also shows a particular shape of the funnel support 309, as part of the inlet 302. It can be seen that the funnel support 309 is conical towards the guide 303. The funnel 322 can easily be located therein, such that any fluid entering the funnel 322 will flow towards the guide 303.

Figure 25:
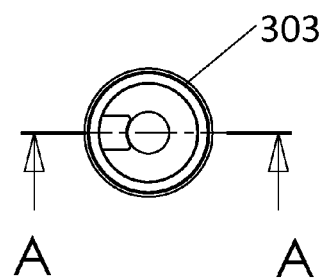
FIG. 25 shows a bottom view of the element of FIG. 23 according to arrow XXV.

FIG. 25 shows a bottom view of the element of FIG. 23 according to arrow XXV. This figure resembles FIG. 8 of the first embodiment.

Figure 26:
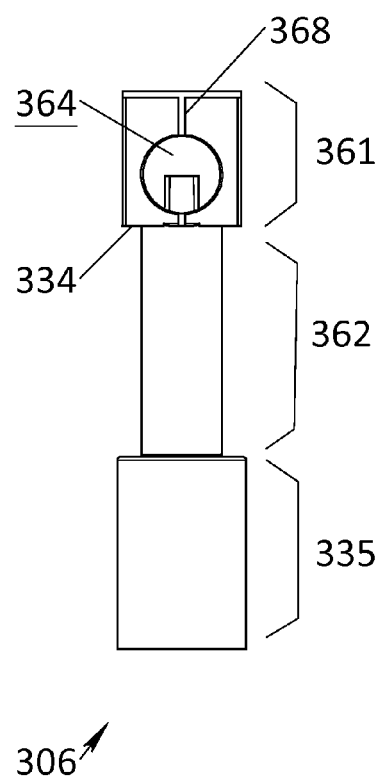
FIG. 26 shows a right side view of the element of FIG. 23 according to arrow XXVI.

FIG. 26 shows a right side view of the element of FIG. 23 according to arrow XXVI. This figure resembles FIG. 10 of the first embodiment, and shows a.o. the first opening 364 for receiving the first liquid portion. One can also see that the element 306 has ribs 368, and a third segment 335.

Figure 27:
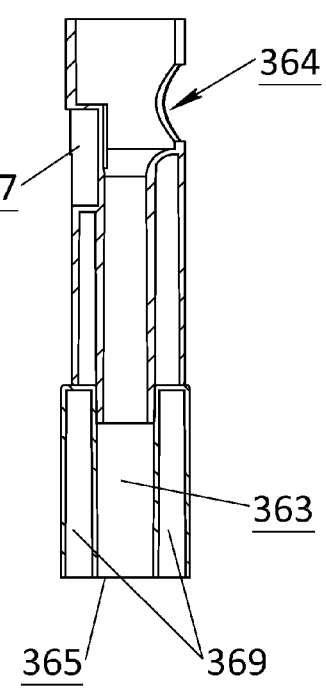
FIG. 27 shows a cross-section of the element of FIG. 25 in the plane A-A.

FIG. 27 shows a cross-section of the element of FIG. 25 in the plane A-A. This figure resembles FIG. 11 of the first embodiment. The element 306 comprises a first channel 363 between a first opening 364 and a second opening 365 for directing the first liquid portion from the inlet 302 towards the reservoir 305. The element 306 also has at least one air chamber 369 located at a lower portion of the element 306 for lifting the element 306 as the reservoir 305 is being filled. The air chamber 369 is formed by the third segment 335. Instead of having two openings and an internal second channel, the element 306 has a trench 367, which however performs the same function, namely providing an open or closed air channel, when the element 6 is present in the guide 303.

Figure 28:
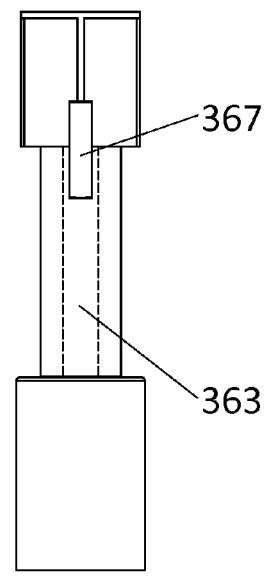
FIG. 28 shows a left side view of the element of FIG. 23 according to arrow XXVIII.

FIG. 28 shows a left side view of the element of FIG. 23 according to arrow XXVII, and shows again the trench 367.

Figure 29:
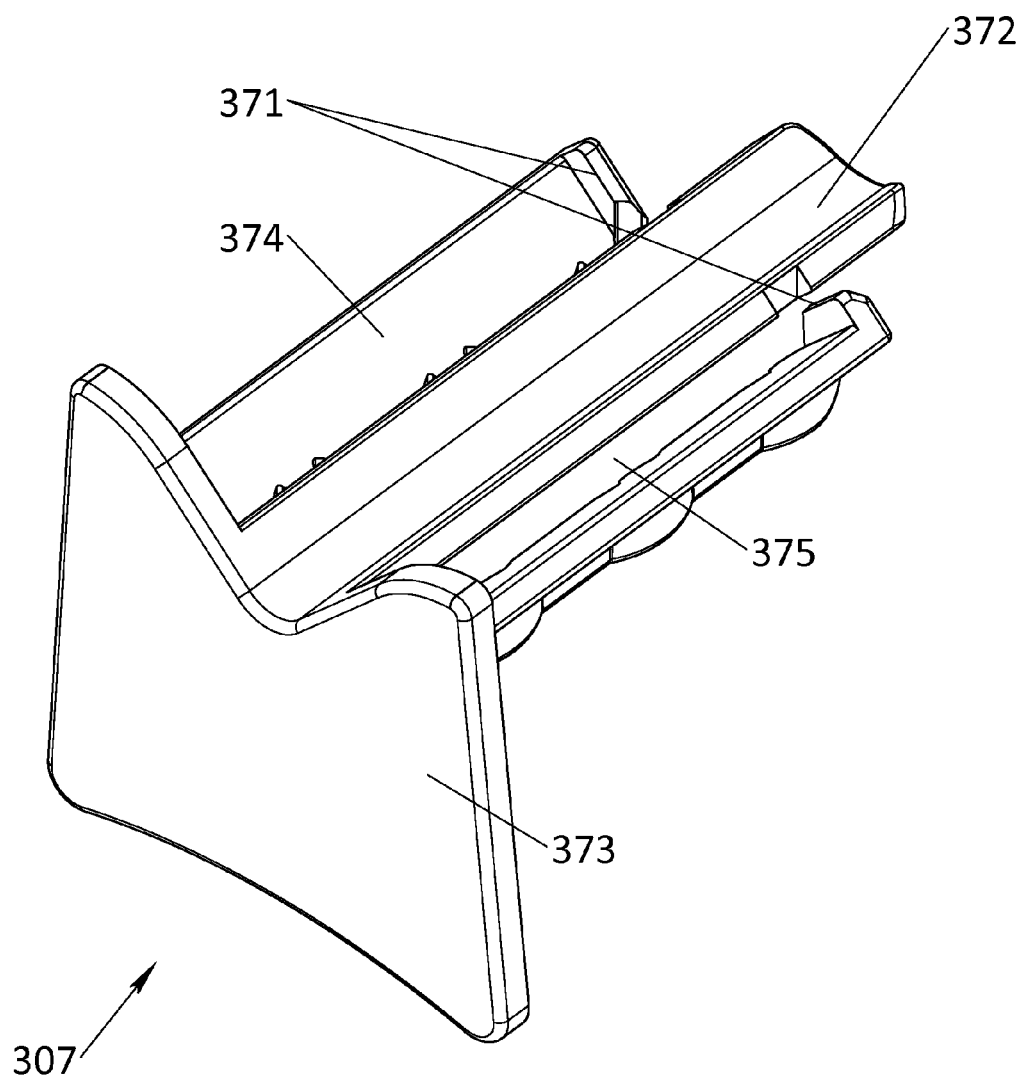
FIG. 29 shows the clip of FIG. 20 in enlarged perspective view.

FIG. 29 shows the clip 307 of FIG. 20 in enlarged perspective view. It comprises a planar portion 373 and three elongated portions located inclined thereto, e.g. substantially perpendicular thereto. The portion 372 is referred to as "funnel holder" 372, the other two portions are referred to as "two arms" 374, 375. The arms are located substantially parallel to the funnel holder 372 and at a distance therefrom. The funnel 322 can then be inserted between the funnel holder 372 and the two arms 374, 375. An end portion of each arm 374, 375 comprises a clip snap 371 for engaging in one of the openings 392, 391 of the funnel support 309, as shown in FIG. 21, and as will be further explained next.

FIG. 30 shows the funnel 322 and the clip 307 and part of the funnel support 309 of FIG. 20, mutually engaged in a first mounting position, referred to as the "transportation mode". FIG. 30 shows the clip 307 after insertion of its arms 374, 375 in the so called mounting slots 393 of the funnel support 309 (see FIG. 21), and after engagement of the clip snaps 371 in the openings 392, referred to as "transportation slots". In this mode, the funnel 322 is typically partly folded and is mounted to the funnel support 309 by means of the clip 307.

FIG. 31 shows the funnel 322 and the clip 307 and part of the funnel support 309 of FIG. 30, after pushing of the clip 307 in the direction of the guide 303 (right of the figure), until the planar portion 373 of the clip 307 contacts the clip plane 394 of the funnel support 309. This will bring the funnel 322 into its operational position, i.e. well-fitting to the inlet 302 and providing sufficient opening (e.g. sufficient width, in a direction perpendicular to the plane of the drawing). In this configuration, the clip 307 and the funnel support 309 are mutually engaged in a second mounting position, referred to as the "activation mode". As can be seen from FIG. 31, the clip snaps 371 (only one of which is visible) are engaged in the openings 391, referred to as "locking slots". In this mode, the funnel 322 is folded open, and well inserted into the conical inlet 302, and the device 301 is ready for capturing a first portion of a liquid flow.

Even though the devices are described above in the context of capturing urine, other applications are also envisioned, such as e.g. capturing a fraction of dumped waste water.

Although several changes can be observed between the device 1 of the first embodiment and the device 301 of the fourth embodiment, other embodiments, although not described, are also contemplated. Such other embodiment, may include one or more of the additional features described in the fourth embodiment, e.g. longitudinal ribs 368, and/or separate funnel 322, and/or linear edge portion for correctly inserting the movable element into the guide, and/or a clip mountable or mounted to the funnel.

The invention claimed is:

1. A device for capturing a first portion of a liquid flow, the device comprising:
    an inlet for receiving the liquid flow;
    an outlet for draining an excess of the liquid flow;
    a guide connected between the inlet and the outlet, and adapted for directing the first portion of the liquid flow towards a reservoir connected to the guide and for directing a subsequent portion of the liquid flow to the outlet;
    wherein the guide comprises a displaceable element adapted for creating passage of liquid between the inlet and the reservoir while blocking passage of liquid between the inlet and the outlet when the displaceable element is in a first position, and for blocking passage of liquid between the inlet and the reservoir while creating passage of liquid between the inlet and the outlet when the displaceable element is in a second position, the displaceable element comprising lifting means for displacing the displaceable element from the first to the second position when the first portion of the liquid flow is captured in the reservoir.

2. The device according to claim 1, wherein the displaceable element is an elongated element movable in a direction substantially transverse to the direction from the inlet to the outlet.

3. The device according to claim 1, wherein the lifting means comprises a predefined volume of a material having a mass density lower than that of the liquid to be captured.

4. The device according to claim 1, wherein the lifting means comprise at least one air chamber.

5. The device according to claim 1, wherein:
    the displaceable element has a first segment with a first cross section, and a second segment with a second cross section smaller than the first cross section, and a first channel extending from a first opening in the first segment to a second opening in the second segment, such that when in the first position the first opening is in fluid connection with the inlet for receiving the first portion of the liquid flow so as to direct the first portion through the first channel towards the reservoir, and such that when in the second position the first opening is blocked from the inlet while the smaller cross section of the second segment allows passage of the second fluid portion from the inlet to the outlet; and
    the guide has an internal edge complementary to the second cross section.

6. The device according to claim 5, wherein the displaceable element further comprises a second channel arranged for allowing air to escape from the reservoir into the outlet during capturing of at least a fraction of the first portion of the liquid flow when the displaceable element is in the first position, and arranged such that passage of liquid from the outlet to the reservoir is blocked when the displaceable element is in the second position.

7. The device according to claim 1, wherein:
    the guide has a first opening arranged between the inlet and the reservoir, and the displaceable element has a protrusion adapted for blocking the first opening when in the second position while leaving the first opening open when in the first position for receiving the first fluid portion;
    the displaceable element has an upper segment with a closed wall section and a lower segment with a narrowing or a second opening arranged such that the closed wall section blocks passage of liquid from the inlet to the outlet when in the first position for directing the first fluid portion towards the reservoir, while allowing passage of the second fluid portion from the inlet to the outlet when in the second position.

8. The device according to claim 1, further comprising a second guide and a second movable element and a second reservoir for capturing a second portion of the liquid stream.

9. The device according to claim 1, wherein the inlet comprises a funnel, wherein the funnel is made of a material which can be reversibly folded and unfolded or reversibly snap-compressed and decompressed.

10. The device according to claim 1, wherein the device is at least partly made of biologically degradable material or of polymers.

11. The device according to claim 1, furthermore comprising readout means for reading out a result of a test performed on liquid captured in the reservoir.

12. A kit of parts, comprising:
    a tubular inlet;
    a tubular outlet;
    a guide having at least three openings, a first opening connectable to the tubular inlet, a second opening connectable to the tubular outlet, a third opening connectable to a reservoir;
    an element displaceable in the guide, and adapted for creating passage for liquid between the inlet and the reservoir while blocking passage of liquid between the inlet and the outlet when the displaceable element is in a first position, and for blocking passage of liquid between the inlet and the reservoir while creating passage for liquid between the inlet and the outlet in a second position, the displaceable element comprising lifting means.

13. The kit of parts according to claim 12, wherein two or more parts selected from the tubular inlet and the tubular outlet and the guide are combined in a monolithic part.

14. The kit of parts according to claim 12, further comprising a reservoir.

15. The kit of parts according to claim 14, wherein the reservoir comprises a DNA stabilization agent, or a preservation liquid.

16. The kit of parts according to claim 12, further comprising a funnel and a clip for mounting the funnel to the inlet and/or for holding the funnel in an unfolded or decompressed state and/or for allowing the assembled parts to stand in an upright position on a substantially horizontal surface.

17. Method for assembling a device for capturing a first portion of a liquid flow, the method comprising:
    providing an inlet for receiving the liquid flow; an outlet for draining an excess of the liquid flow; and a guide adapted for directing the first portion of the liquid flow towards a reservoir connected to the guide and for directing a subsequent portion of the liquid flow to an outlet; wherein the guide comprises a displaceable element adapted for creating passage of liquid between the inlet and the reservoir while blocking passage of liquid between the inlet and the outlet when the displaceable element is in a first position, and for blocking passage of liquid between the inlet and the reservoir while creating passage of liquid between the inlet and the outlet when the displaceable element is in a second position, the displaceable element comprising lifting means for displacing the displaceable element from the first to the second position when the first portion of the liquid flow is captured in the reservoir;
    if the inlet is separate from the guide, connecting the inlet to the guide;

if the outlet is separate from the guide, connecting the outlet to the guide;

connecting the reservoir to the guide;

inserting the displaceable element in the guide, the displaceable element being adapted for creating passage of liquid between the inlet and the reservoir while blocking passage of liquid between the inlet and the outlet when the displaceable element is in a first position in the guide, and for blocking passage of liquid between the inlet and the reservoir while creating passage of liquid between the inlet and the outlet when the displaceable element is in a second position in the guide.

18. The method according to claim 17, further comprising:

connecting a cap to the guide.

19. The method according to claim 17, further comprising:

connecting a funnel to the inlet.

20. The device according to claim 5 wherein the cross-section of the first segment is circular, and the cross section of the second segment is elliptical, and wherein the guide has a corresponding elliptical edge.

* * * * *